US010973754B2

(12) United States Patent
Herrlein et al.

(10) Patent No.: US 10,973,754 B2
(45) Date of Patent: Apr. 13, 2021

(54) DUAL POLYMER COMPONENT HAIR COLORING COMPOSITION

(71) Applicants: Coty Inc., New York, NY (US); HFC Prestige International Holding Switzerland S.a.r.l, Petit-Lancy (CH); Mathias Kurt Herrlein, Kronberg (DE); Matija Crne, Wiesbaden (DE); Simon Paul Godfrey, Oberursel (DE); Graham Mckelvey, Schwalbach (DE); Lars Siegfried Dahne, Berlin (DE); Ingo Weber, Gruenstadt (DE); Markus Speckbacher, Mettenheim-Hart (DE); Mandy Hecht, Falkensee (DE)

(72) Inventors: Mathias Kurt Herrlein, Kronberg (DE); Matija Crne, Wiesbaden (DE); Simon Paul Godfrey, Oberursel (DE); Graham Mckelvey, Schwalbach (DE); Lars Siegfried Dahne, Berlin (DE); Ingo Weber, Gruenstadt (DE); Markus Speckbacher, Mettenheim-Hart (DE); Mandy Hecht, Falkensee (DE)

(73) Assignee: WELLA OPERATIONS US, LLC, Calabasas, CA (US)

( * ) Notice: Subject to any disclaimer, the term of this patent is extended or adjusted under 35 U.S.C. 154(b) by 0 days.

(21) Appl. No.: 16/488,007

(22) PCT Filed: Oct. 5, 2018

(86) PCT No.: PCT/US2018/054724
§ 371 (c)(1),
(2) Date: Aug. 22, 2019

(87) PCT Pub. No.: WO2019/071207
PCT Pub. Date: Apr. 11, 2019

(65) Prior Publication Data
US 2020/0093730 A1 Mar. 26, 2020

Related U.S. Application Data

(60) Provisional application No. 62/652,231, filed on Apr. 3, 2018, provisional application No. 62/652,256, filed on Apr. 3, 2018, provisional application No. 62/694,781, filed on Jul. 6, 2018, provisional application No. 62/694,816, filed on Jul. 6, 2018, provisional application No. 62/694,734, filed on Jul. 6, 2018, provisional application No. 62/694,808, filed on Jul. 6, 2018, provisional application No.
(Continued)

(30) Foreign Application Priority Data

Oct. 6, 2017 (EP) ..................... 17195273
May 3, 2018 (EP) ..................... 18170717

(51) Int. Cl.
A61K 8/898 (2006.01)
A61K 8/81 (2006.01)
A61Q 5/10 (2006.01)

(52) U.S. Cl.
CPC .............. *A61K 8/898* (2013.01); *A61K 8/817* (2013.01); *A61K 8/8111* (2013.01); *A61K 8/8135* (2013.01); *A61K 8/8158* (2013.01); *A61Q 5/10* (2013.01)

(58) Field of Classification Search
CPC .... A61K 8/898; A61K 8/8111; A61K 8/8135; A61K 8/8158; A61K 8/817; A61K 8/8147; A61K 8/8194; A61K 8/84; A61K 2800/5424; A61K 8/5426; A61K 2800/884; A61Q 5/10; A61Q 5/065
See application file for complete search history.

(56) References Cited

U.S. PATENT DOCUMENTS

2008/0108740 A1  5/2008  Evers
2010/0088036 A1  4/2010  Goddard-Clark et al.

FOREIGN PATENT DOCUMENTS

DE   199113625 A1   9/2000
EP   0132960 A2    2/1985
(Continued)

OTHER PUBLICATIONS

"European Application Serial No. 17195273.2, Extended European Search Report dated Jan. 11, 2018", 8 pgs.
(Continued)

*Primary Examiner* — Carlos A Azpuru
(74) *Attorney, Agent, or Firm* — Victoria Friedman; Dennemeyer & Associates, LLC

(57) ABSTRACT

The instant disclosure generally relates to a dual component hair coloring composition for coloring mammalian or synthetic keratin fibers, the composition comprising composition A comprising a cationic polymer, pigment microparticles and an aqueous medium, and comprising composition B comprising an anionic polymer, aqueous medium and optional cross linking agent. Optionally or alternatively composition B may contain pigment particles. The cationic and anionic polymers are at least partially soluble in the medium and the pigment microparticles are dispersed therein. The hair coloring composition forms a dual layer coating upon application to keratin fibers such as hair and has a substantially permanent pigment lastingness following development (setting); minimally alters the keratin fibers, upon application; and substantially eliminates development time. Methods of using such compositions are also described herein.

21 Claims, No Drawings

Related U.S. Application Data

62/696,301, filed on Jul. 10, 2018, provisional application No. 62/739,672, filed on Oct. 1, 2018.

(56) References Cited

FOREIGN PATENT DOCUMENTS

| WO | 2009/073759 | * | 6/2009 |
|---|---|---|---|
| WO | 2009/073759 A1 | * | 6/2009 |
| WO | WO-2009073759 A1 | | 6/2009 |
| WO | WO-2019071207 A1 | | 4/2019 |

OTHER PUBLICATIONS

"International Application Serial No. PCT/US2018/054724, International Search Report dated Feb. 26, 2019", 6 pgs.

"International Application Serial No. PCT/US2018/054724, Invitation to Pay Additional Fees Partial Search Report dated Jan. 3, 2019", 12 pgs.

"International Application Serial No. PCT/US2018/054724, Written Opinion dated Feb. 26, 2019", 9 pgs.

Barber, David, et al., "A Logical Stepwise Approach to Laser Diffraction Particle Size Distribution Analysis Methods Development and Validation", Pharmaceutical Development Technology, 3(2), (1998), 153-161.

"International Application Serial No. PCT/US2018/054724, International Preliminary Report on Patentability dated Apr. 16, 2020", 9 pgs.

* cited by examiner

DUAL POLYMER COMPONENT HAIR COLORING COMPOSITION

PRIORITY

This application is a U.S. National Stage Filing under 35 U.S.C. 371 from International Application No. PCT/US2018/054724, filed on Oct. 5, 2018; and published as WO 2019/071207 on Apr. 11, 2019, which application claims the benefit of priority from EP patent application Serial No, EP 17195273, filed Oct. 6, 2017; EP patent application Serial No. EP 18170717, filed May 3, 2018; and U.S. provisional patent applications Ser. No. 62/652,231, filed Apr. 3, 2018; Ser. 62/652,256 filed Apr. 3, 2018; Ser. 62/694,781 filed Jul. 6, 2018; Ser. 62/694,816, filed Jul. 6, 2018; Ser. 62/694,734 filed Jul. 6, 2018; Ser. 62/694,808 filed Jul. 6, 2018; Ser. 61/696,301 filed Jul. 10, 2018 and Ser. 62/739,672 filed Oct. 1, 2018, all of which are incorporated herein by reference in their entirety.

BACKGROUND

Treatments to mammalian or synthetic keratin fibers, and their surfaces, are well known in the art. Of particular note are treatments that alter the color appearance of the hair or provide other colored or reflective properties through surface treatment of the hair; dissolution (absorption) of dye molecules into the keratin fiber or attachment to the fiber surface (so called direct dyes); and/or dissolution of dye precursors into the keratin fiber, followed by reaction of these dye precursors within the hair to form dye species (so called oxidative dyeing). Surface coloration treatments and many soluble dyes can be later washed out. Alternatively, pigments can be adhered to the hair surface to alter the perceived color.

One drawback of the known oxidation based technologies in this area is that the methods for applying dye based coloring materials involves compositions that can irritate the scalp, for example such compositions may contain ammonia (often as ammonium hydroxide) or monoethanolamine combined with hydrogen peroxide. This prevents the hair coloration experience from being pleasant or a so called wellness experience. Such coloring compositions also alter the hair structure itself, leading to oxidation of the hair surface, and partial degradation to the keratinous proteins from which the hair structure is constructed. With repeated coloring, these changes in hair structure become more pronounced. The color obtained when coloring with such composition is hard to predict, and even highly experienced users can still be surprised with the results that are obtained. Yet another drawback to known technologies is that, once the color is on the hair, the dye based coloring material is difficult to remove and/or cannot be completely removed. A drawback of pigment based coloring approaches is the low adherent fastness of the pigment or colored material to the keratin fibers. This results in the pigment based color effectively being removed after a single hair wash. Another drawback for both dye and pigment based approaches is that the application of hair coloration materials often yields uneven results as (1) adherence and or penetration of hair coloration materials to the hair surface or within the hair can vary with hair type for example due to changes in porosity, changes in surface composition due to proximity to scalp and/or age of the user; and (2) even when material is adhered or penetrated into the hair, differences in coloration of the underlying hair, including presence of pheomelanin and eumelanin, may yield different color results, even when the same color pigments or dyes are applied across hair types/colors having different native characteristics. There is therefore a need for compositions and methods that not only make the hair coloring experience a beauty/wellness experience, but also address, among other things, the foregoing drawbacks of known technologies.

There is a need for a method for achieving a predetermined target colour in a more reproducible and reliable manner independently from the user's initial hair colour and hair condition. This method should preferably involve the use of compositions which are less aggressive for the hair and for the scalp. This method should also preferably involve the use of low odour compositions.

At least some of these needs may be met by the method for treating hair according to the present invention, wherein a composition comprising at least one pigment is applied onto the hair to impart the hair with an intermediate colour which is different to the initial colour, and subsequently, a second composition is applied onto the hair to enable desirable characteristics including but not limited to extension of the duration of the coloring without fading or ameliorating intensity.

SUMMARY

According to aspects of the invention, the dual component hair coloring composition, method and coated hair embodiments provide a surface coloration of hair strands that may be substantially uniform to significantly varied, may give strands an appearance of a muted, brilliant, shiny or reflective nature. These aspects provide color fastness during a series of washes with shampoo or soap yet with appropriate formulations can be readily removed to leave the natural shade of the hair. These aspects significantly lessen and/or avoid treatment of hair that may cause breakage of keratin protein intermolecular bonds.

An aspect of the invention concerning the hair coloring composition with optional in situ components provides embodiments comprising a dual step and dual component and dual layer coloration to the surfaces of hair strands. The dual steps involve a first application of composition A comprising at least a cationic polymer and a second application of composition B comprising at least an anionic polymer. Composition A and/or composition B will contain pigment microparticles. Preferably, the first component of the dual component hair coloring composition is composition A which comprises pigment particles optionally coated with adherent material, a cationic polymer and an aqueous medium optionally also containing an alcohol. The preferred second component of the dual component hair coloring composition is composition B which comprises an anionic polymer such as a carboxylic acid polymer which is dissolved or dispersed in an aqueous medium. The component compositions are sequentially applied to the hair and optionally and preferably dried after each application. The component compositions preferably are soluble in aqueous medium. The medium may be water or a mixture of water and a polar, protic or aprotic organic solvent. The pigment microparticles of composition A and/or composition B may comprise irregular shapes of at least one pigment color and have at least one dimension of less than one micron. Composition B may also optionally comprise a cross linking agent which will combine in situ with the anionic polymer such as a carboxylic acid polymer or copolymer on the hair to provide a partially cross linked polymer film.

According to a second aspect, the hair coloring composition includes a first composition A comprising a cationic polymer and an aqueous medium, and a second composition B comprising an anionic polymer and an aqueous medium. The composition A can contain pigment particles according to the preferred embodiments described herein. Alternatively, composition B can contain pigment particles according to embodiments described herein. It is also possible that both composition A and composition B contain pigment particles. The pigment particles contained in composition A and composition B can be the same or can be different.

Preferably the cationic polymer of composition A may be formulated in protonated form or may be quaternized. Preferably the anionic polymer of composition B may be formulated as a corresponding salt such as an ammonium salt. The cationic polymer of composition A and the anionic polymer of composition B can be solubilized at least to some extent in water.

Embodiments of the cationic polymer of composition A may comprise a polymeric amine. The polyamine may comprise organic or silicone polymers containing pendant amine groups and/or amine groups within the polymer chain. The polymer may be linear or branched. The ratio of amine groups to polymer chain length may be determined by the amine number. The nitrogen number may range in molar percent per chain atom from as little as 1 to 5 mole percent to as much as 50 mole percent. The maximum nitrogen number possible is 50 mole percent in this context. For example, a polyvinylamine will have one nitrogen per two carbons of each vinyl monomer so that the nitrogen number in mole percent will be 50 percent. Preferably, the amine number in mole percent may range from about 10 mole percent to about 50 mole percent, more preferably about 15 mole percent to about 50 mole percent, most preferably about 25 to 50 mole percent. Examples of cationic polymer include but not limited to polyethyleneimine, polyaminosilicone, polyallylamine hydrochloride, polydialllyldimethylammonium chloride, polyvinylamine, copolymers thereof, mixtures thereof and block copolymers thereof as well as the protonated and quaternized versions thereof. The cationic polymer may have a weight average molecular weight ranging from about 0.5 kDa, preferably from 0.5 kDa to 5000 kDa, more preferably from 2 kDa to 1000 kDa, even more preferably from 10 kDa to 200 kDa, most preferably from 25 kDa to 70 kDa.

Embodiments of the anionic polymer or copolymer of the composition B may comprise an olefinic acid such as an olefinic carboxylic acid polymer or an olefinic carboxylate ester in forms such as a homopolymer, copolymer or terpolymer, all of which have pendant carboxylic acid moieties and/or carboxylate ester moieties. The carboxylic acid polymer may comprise a vinyl polymer, a polybutadiene, a polyisoprene, a polyurethane, a polyacrylonitrile, a poly(meth)acrylate all with at least multiple pendant carboxyl groups. The homopolymers, copolymers and/or terpolymers of the carboxylic acid polymer may have an acid value ranging from about 0.01 to about 700, about 3 to about 500, more preferably about 3 to about 200, especially more preferably about 25 to 175, most preferably about 40 to about 200, with a favored upper range of up to about 170. In addition to the carboxylic acid monomer, the copolymer and terpolymer may include neutral olefinic monomers. Embodiments of the carboxylic acid polymer or copolymer component may be neutralized with a base to provide enhanced solubility of the carboxylic acid polymer in the medium. The homopolymers, copolymer and/or terpolymers may have a weight average molecular weight ranged from about 500 Da to about 1 MDa, preferably about 500 Da to about 500 kDa, more preferably about 1 kDa to about 200 kDa and most preferably about 1 KDa to about 200 kDa.

Embodiments of the cross linking agent component may comprise functional organic compounds that have at least dual functional groups. The cross linking agent is designed to form esters, amides, ureas, urethanes, or stable complexes with the carboxylic acid groups of the carboxylic acid polymer or copolymer. Exemplary cross linking agents include polyols, polyamines, polycarbodimides, polyisocyanates, glutaraldehyde and multivalent complexed metal salts. The cross linking agent may have two, three, four or more groups that will combine with the carboxylic acid groups.

Embodiments of the pigment microparticles used on the hair coloring formulation described herein may comprise organic pigment microparticles, which imparts color to the hair, having a given D50[vol], and pigment microparticles, for providing light scattering properties to the colored hair, having a D50[vol] which is larger than the D50[vol] value of the organic pigment microparticles. Embodiments include a mixture of organic pigment microparticles having a D50[vol] of about 0.06 micron to about 0.18 micron, preferably of about 0.08 micron to about 0.15 micron, and light-scattering pigment microparticles having a D50[vol] of about 0.15 micron to about 0.3 micron, preferably of about 0.16 micron to about 0.25 micron.

The aspect of the invention concerning the method for combining the hair coloring composition with hair strands comprises applying composition A to the hair and at least partially drying composition A on the hair so that it will not be removable by wiping and subsequently applying composition B to the hair and drying the dual layer composition on the hair. If an in situ cross linking agent is included in composition I3, the drying step may also include drying with heat to promote the cross linking reaction. The multiple drying steps substantially to essentially remove and/or eliminate the medium from the composition before proceeding to the next step. The resulting coating embodiments on the hair strands comprise a dual layer coating of a first layer of the cationic polymer with pigment, and a second layer of anionic polymer optionally with at least partial cross linking. The coating embodiments have a thickness of from about 50 nm to 3 microns, preferably 150 nm to 5 microns. The pigment microparticles are somewhat to substantially uniformly distributed in the first layer of the coating. Although it is not a limitation of the invention, upon their combination on the hair, it is believed that the cationic polymer and anionic polymer may interact to form electrostatically combined interpolymer materials which may be viewed as complex salts. Because the hair strands are thought to be negatively charged, it is also believed that this same interaction occurs between the cationic polymer and the hair strands.

In addition to the above described components of compositions A and B, these compositional components of the hair coloring composition may optionally contain additional components in this mixture. These additional components include but not limited to one or more of dispersants, surface treatment agents for the pigment microparticles, plasticizers, conditioners, suspending agents, thickening agents, adjuvants, moisturizers, surfactants, fatty substances, waxes, fatty amides and soluble organic dyes of colors different from those of the pigment microparticles. The hair coloring composition consequently may contain a number of components that add to the total solids content of the composition. Generally, for application to human hair, the hair coloring composition may have a total solids content ranging from about 1 wt % to about 40 wt %, preferably about 2 wt % to about 30 wt %, more preferably about 4 wt % to about 20 wt % relative to the total weight of the composition.

The aspect of the invention concerning the fastness of the coating on the hair strands comprises the ability of the coating to somewhat to substantially resist dissolution by ordinary cleaning of the hair. Ordinary cleaning of the hair may involve washing with soap and water, washing with an aqueous dilution of shampoo and washing with water.

The aspect of the invention concerning removal of the coating on the hair strands comprises application of a medium of a trigger formulation designed to remove the coating. The trigger formulation embodiments of the invention comprise a medium with a base. Embodiments of the base include organic and inorganic compounds that provide a stronger basic medium than does a dilute aqueous mixture of soap or a shampoo containing an anionic surfactant. Included are aqueous solutions or mixtures of ammonia, trialkyl amine of from one to four carbons in each alkyl group, dialkylamino alkyl alcohols of from one to four carbons in each of the dialkyl groups and two to four carbons in the alkyl group, alkanolamines such as monoethanolamine, diethanolamine and triethanolamine, bicarbonate or carbonate of alkali or alkaline earth metal salts, acetaldehyde ammonia trimer, alkali or alkaline earth metal hydroxides and/or alkaline earth metal halide complexes with trialkyl amine described above.

An additional aspect of the invention concerns the application of the hair coloring composition to keratin tissue such as brows, lashes, nails and skin as well as to hair on the scalp. For such applications to keratin tissue, the hair coloring composition becomes a color composition. The color composition may be applied to the hair of eyebrows and eye lashes with appropriate adjustments of the composition parameters within the parameters described for hair on the scalp. Typically, the eyebrow hair may be treated with the color composition using parameters similar to or the same as those of the hair coloring composition for hair on the scalp. The hair of eyelashes typically can be similarly treated with the color composition for eyebrows and the viscosity adjusted to provide a somewhat more viscous color composition for application to the eye lashes. For nails and skin, the parameters of the color composition may be similar to those of the hair coloring composition and viscosity adjusted to provide embodiments that will not readily drip or otherwise flow off the nail or skin surface to which the color composition is applied. The color composition for nails and skin will be in situ cross-linked to provide a durable coating or covering on the keratin nail and skin substrate.

DEFINITIONS

Unless defined otherwise, all technical and scientific terms used herein have the same meaning as commonly understood by a person of ordinary skill in the art.

As used in the specification and the appended claims, the singular forms "a," "an" and "the" include plural referents unless the context clearly dictates otherwise The term "may" in the context of this application means "is permitted to" or "is able to" and is a synonym for the term "can." The term "may" as used herein does not mean possibility or chance.

The term "flake factor" means (weight percent active flake in composition)/(flake thickness in microns)

The term and/or in the context of this application means one or the other or both. For example, an aqueous solution of A and/or B means an aqueous solution of A alone, an aqueous solution of B alone and an aqueous solution of a combination of A and B.

The terms (meth)acrylic acid and (meth)acrylate mean herein both of the acrylic acid and methacrylic acid and both of the acrylate methacrylate esters. The parenthesis surrounding the prefix "meth" means that the term (meth) acrylic encompasses both of the methacrylic acid and acrylic acid monomers. This term has the same meaning when used with polymers. Without a parenthesis, the term "methacryl" means only the methacrylic acid and esters and does not include acrylic acid and esters. The suffix "ate" means that the term (meth)acrylate is an ester formed by combination of a monoalcohol or diol with methacrylic acid or acrylic acid.

Acid value or acid number used according to the invention means the mass of potassium hydroxide (56 g per mole) in milligrams that is required to neutralize one gram of the substance being investigated. The formula is X mg KOH=AV wherein X mg is the amount of KOH needed to neutralize 1 gram of test substance. Because the calculation is always based upon 1 gram of the test substance, if it is assumed that the test substance contains a mole of acid per mole of test substance, the number of moles of test substance in this 1 gram decreases as the molecular weight increases. Hence the AV decreases for this kind of acid material as its molecular weight increases. For example, the AV of benzoic acid (mw of 122) (1 g/122 g per mole×56 g per mole×1000 mg/g) is 459 while the AV of naphthoic acid (mw of 178) (56/178×1000 mg/g) is 315. For acidic polymers, an acid value will not usually provide its molecular weight because the polymer usually will be composed of units other than acid. Nevertheless, molecular weight calculation of an acidic polymer can be made if it is composed only of acid monomers. For example, the acid number of acrylic acid (mw of acrylic acid is 72 g/mol) is determined by the calculation as follows: (1 g/72 g mol$^{-1}$×56 g mol$^{-1}$)=0.778 gm of KOH. This number in milligrams is 778 mg which provides the acid number of 778. With a dimer of acrylic acid this acid number is halved (1 g/144×56 g m$^{-1}$)=389. This demonstration shows that the acid value (AV) of polyacrylic acid will decrease as the weight average molecular weight of the polyacrylic acid increases. At an acid number of 97.2 for a polyacrylic acid, the apparent mw would be 56/0.0972 or 576 g per mole. This would provide an oligomer of 8 acrylic acid monomers per mol.

The molecular weight of a polymer or oligomer used according to the invention may be measured by a weight average molecular weight, and the distribution of molecules of different molecular weights of a polymer or oligomer used according to the invention is determined by its polydispersity index. Molecular weight is expressed as daltons (Da), kiloDaltons (kDa) and megaDaltons, which is million daltons or (MDa). The acronym Mw stands for weight average molecular weight, Mn is the number average molecular weight of a given polymer. Polydispersity is a unit-less number and indicates the breadth of the distribution of the polymer molecular weights and is defined as the Mw/Mn.

The term "about" is understood to mean ±10 percent of the recited number, numbers or range of numbers.

The term "about 0 wt %" is understood to mean that no substance, compound or material to which zero (0) refers is present, up to a negligible but detectable amount is present, assuming that the detectability can be determined on a parts per million basis.

The term "hydrogen bonding" is understood to mean a compound or group that contain a hydroxyl group or a hydrogen that is part of a polar group, such as but not limited to an amine, a carboxylic acid, a urethane group, a urea group and other similar groups and that can form molecule to molecule interaction through electrostatic or ionic interaction between positive and negative dipolar or ionic groups.

In addition, where features or aspects of the invention are described in terms of Markush groups, those skilled in the art will recognize that the invention is also thereby described in terms of any individual member or subgroup of members of the Markush group. For example, if X is described as selected from the group consisting of methyl, ethyl or propyl, claims for X being methyl and claims for X being methyl and ethyl are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4. Similarly, values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3?, and 4%) and the sub-ranges (e.g., 0.1% to 0.5%, 1.1% to 2.2%, 3.3% to 4.4%) within the indicated range.

Hair and hair strands mean natural or synthetic keratin fibers. Hair, hair strands and keratin fibers are used interchangeably in this document. Natural keratin fibers include those from mammals and/or on mammals including human, primate, ruminant, camelid, equine, rodent and neovison including but not limited to cow, sheep, deer, goat, buffalo, lama, alpaca, camel, guanaco, vicuna, horse, antelope, moose, elk, rat, mouse, beaver, rabbit, mink, monkey, ape and similar species. Synthetic keratin fibers include polyamides, polyacrylic and polyester fibers, especially polyamide fibers which are used for artificial hair implantation.

Homopolymer, copolymer and terpolymer mean polymers having carbon-carbon backbones with side chains of various classes of groups. A homopolymer may have side chains of carboxylic acid or amine groups and optionally some carboxylic acid or amine derivative groups. The homopolymer may be based on a single monomeric unit structure such as acrylic acid or pentadienoic acid or pent-3-enoic acid isoprenoic acid or vinyl amine or aziridine or allyl amine or may be several monomeric unit structures wherein each unit contains at least a carboxylic acid side chain or amine side chain. The copolymer and terpolymer have side chains of carboxylic acid or amine as described above for the homopolymer and also have side chains of esters, amides and side chains such as alkyl groups or aromatic groups or similar groups which not derived from carboxylic acid groups or amine groups. The copolymer may contain two different monomeric units and may contain one or two additional different monomeric units. The terpolymer may contain at least three different monomeric units and may contain multiple different monomeric units.

As used herein, the term "transfer resistance" generally refers to the quality exhibited by compositions that are not readily removed by contact with another material, such as, for example, an item of clothing or the skin. Transfer resistance can be evaluated by any method known in the art for evaluating such. For example, transfer resistance of a composition can be evaluated by the amount of product transferred from a wearer to any other substrate after the expiration of a certain amount of time following application of the composition to the hair. The amount of composition transferred to the substrate can then be evaluated and compared. For example, a composition can be transfer resistant if a majority of the product is left on the wearer's hair. Preferably little or no composition is transferred to the substrate from the hair.

Test Method is defined as the transfer of the composition from the hair can be assessed using the following method. Hair tresses are colored according to the test method described. A white cotton cloth is used to test the composition transfer. The cloth measuring 15 mm by 75 mm is folded in half so as to create two sides with a size of 15 mm by 37.5 mm. Between the two sides the colored hair tress is inserted and laid flat onto a surface such that the top portion of the tress where it is glued together just protrudes from the folded two sides of cotton. A weight of 0.1 Kg is applied evenly over the top surface of the cotton. The hair tress is then pulled through the cotton cloth over a time until it is removed altogether from the cloth in 1 to 3 seconds. The weight is removed, and the cloth opened to reveal the inner surface. A visual assessment can then be performed on the sample to give it a rating from 0 to 5 for color transfer, with 0 being no transfer and 5 being extremely high transfer. The method can also be used to compare between different prototypes and provide a comparative assessment of better or worse performance.

As used herein, the term "minimally alters the keratin fibers, upon application" generally means that after removal of the coloring composition the hair fibers are returned to a substantially unaltered state. The state of the hair can be assessed for example using ATR FT-IR for oxidative damage as described later or through tensile testing methods known to those skilled in the art for assessing hair strength for example using equipment such as those designed and sold by Dia-Stron™.

As used herein, the term "color fastness" means substantial color lastingness or color fastness when the color of the colored hair fibers changes less than 50%, less than 40%, less than 30%, less than 20%, less than 10% after the colored hair fibers are processed through a multi-cycle rinse study. One kind of protocol for determining color fastness is described in the section below titled "Removal of Color Coating".

As used herein, the term "setting" means converting the hair coloring composition to a solid coating through the application of means designed to remove or otherwise separate the medium from the other components of the hair coloring composition so as to leave a solid coating of the dual layer coating containing the other components of the composition.

"Cross linked", "Cross linkable" and "Cross linking" mean respectively (i) bonds formed between molecules to provide chain branching and/or chain extension; (ii) the potential to form bonds between molecules to provide chain branching and/or chain extension and (iii) the present action involving the subject reaction. The first term "cross linked"

means the molecule in its present or current state is already cross linked. The second term "cross linkable" means that the molecule in its present or current state is not yet cross linked but has the capability of becoming cross linked at a future time. The third term means that the reaction takes place at present between two groups that form a cross link bond. Additionally cross linked and cross linkable also refer to electrostatic interaction between positive and negative groups or dipole groups such that a covalent bond is not formed but strong interatom attraction is present.

"in situ" is a latin phase meaning in its original place. In the context of this invention, it means an activity such a cross linking that takes place on the hair.

As used herein, "carboxylic acid polymer" includes any and all olefinic polymers with at least some pendant carboxylic acid groups including homo, co and terpolymers of olefinic carboxylic acids such as (meth)acrylic acid, maleic acid, fumaric acid, itaconic acid, crotonic acid, pentenoic acid pentadienoic acid, isoprenoic acid, partially hydrolyzed polyacrylonitile homo, co and terpolymers of olefinic carboxylate esters of the foregoing olefinic acids which polymers optionally can also include monomeric units of non-carboxylic acid monomers. The corresponding carboxylate ester polymer is the esterified version of a carboxylic acid polymer.

As used herein, "amine polymer" includes any and all olefinic polymers and silicone polymers with at least some pendant amine groups as well as olefinic and silicone polymers having nitrogen atoms in the chain. Homopolymers, copolymers and terpolymers of such amine arrangements alone and/or with other olefinic and/or silicone moieties are included.

DETAILED DESCRIPTION

The instant invention generally relates to addressing drawbacks of known technology for treating mammalian or synthetic keratin fibers by limiting damage to keratin proteins within the fibers, particularly after repeated dying events; facilitating the quantitative or substantially quantitative on demand removal of the color; limiting quick or inconsistent wash-out of the coloring means; limiting irritation of the scalp upon applying known compositions (e.g., containing hydrogen peroxide with either ammonia or monoethanolamine at and an elevated pH); and shortening at least one of the treatment process and post-treatment processes, including drying time. In sum, the present invention is directed to compositions for treating mammalian or synthetic keratin fibers in such a way that the color can be applied and remain on the hair until it is desired to remove the color. This makes the treatment process a wellness experience. It is also desired that the results are predictable, enabling the user to achieve their target hair color result.

The composition, method and coating aspects of the invention are directed to embodiments of a dual component hair coloring composition that are adapted to provide colored coating embodiments on the surfaces of hair strands. The colored coating embodiments have "color fastness" that enables them to remain in somewhat to substantial to essential original composition on the keratin fibers (hair) through at least a series of washings with diluted aqueous media containing soap and/or shampoo. Yet by manipulation of the triggering formulation according to the invention, the coating embodiments can be removed from the hair to leave the hair in its substantially to essentially natural state before application of the hair coloring composition to the hair. The hair coloring composition embodiments minimally alter keratin fibers upon their application to hair strands and the embodiments of the method of application may be accomplished in short times.

The embodiments of the hair coloring composition according to the invention comprise dual component compositions that may be applied sequentially to the hair. The first of the dual component comprises composition A which includes pigment particles, cationic polymer and a medium in which these ingredients are at least dispersed. The cationic polymer may be dispersed or dissolved in the medium and/or may be arranged as a shell or as a material associated with the pigment. The second dual component composition comprises an anionic polymer dissolved or dispersed in an aqueous medium. Embodiments of the anionic polymer include a carboxylic acid homopolymer, copolymer or terpolymer.

Further alternative embodiments of the hair coloring composition according to the invention comprise dual component compositions that may be applied sequentially to the hair. The first of the dual component comprises composition A which includes cationic polymer and a medium in which these ingredients are at least dispersed. The cationic polymer may be dispersed or dissolved in the medium and/or may be arranged as a shell or as a material associated with the pigment. The second dual component composition includes pigment particles, an anionic polymer dissolved or dispersed in an aqueous medium. Embodiments of the anionic polymer include a carboxylic acid homopolymer, copolymer or terpolymer.

The embodiments of the method of application according to the invention comprise sequential application of dual components, composition A and composition B of the hair coloring composition to the hair. Following application of each component, the medium of the applied component is substantially to essentially removed by air flow evaporation and/or elevated temperature evaporation and/or vacuum evaporation and/or any combination thereof. The embodiments of the method of removal according to the invention comprise application of a triggering formulation that includes a basic composition that is stronger than an aqueous soap medium or an aqueous dilution of shampoo.

The Dual Component Hair Coloring Composition

A. Step A. Application of Composition A

The method according to the present invention may comprise a step of providing on at least a portion of the hair, and preferably throughout the hair, one or more cationic polymers as composition A with or without inclusion of pigment. A pretreatment addition of composition A without pigment particles can enhance the adhesion between the hair and the pigment(s) since the polymeric sublayer(s) positioned on the hair can function as "glue" between the hair and the pigment(s). Irrespective of whether a pretreatment is applied or the cationic polymer is combined with the pigment and medium and applied as the first component to the hair, the cationic polymer can enhance the adhesion between the pigment(s) and hair fibers for the following reasons. Hair is naturally negatively charged. Therefore, the final shell layer of the coated hair which is positively charged can easily attach to the surface of the hair.

Pretreatment may be carried out prior to application of the full composition A. Pretreatment may be carried out immediately prior to application of full composition A (hereinafter full step A), or at least 1 hour prior to full step A), or at least 24 hours prior to full step A), or at least 10 days prior to full step A), or at least one month prior to full step A).

Composition A, Pigment and Cationic Polymer

As mentioned above, the cationic polymer and pigment of composition A may be separately dispersed in the medium of composition A and/or the cationic polymer may be at least in part associated with the pigment particles. The association may be as a coating at least in part on the pigment particle surfaces or may be a core and shell arrangement. The form, style, color and arrangement of the pigment particles are described in the pigment particle section below.

Composition A, the Cationic Polymer

The cationic polymer may be made of one or more cationic polymer(s). The cationic polymer(s) may comprise one or more amino functional group(s) per polymer chain, wherein the amino functional group(s) are selected from the group consisting of primary, secondary, tertiary, quaternary amino functional groups and mixtures thereof, preferably from the group consisting of secondary, tertiary, quaternary amino functional groups and mixtures thereof, more preferably from quaternary amino functional groups.

The cationic polymer(s) may be selected from the group consisting of polyethyleneimine, polyallylamine hydrochloride, polydiallyldimethylammonium chloride, polyvinylamine, copolymers thereof and mixtures thereof. The cationic polymer(s) may preferably be selected from the group consisting of polyethyleneimine, polydiallyldimethylammonium chloride, copolymers thereof and mixtures thereof.

The copolymers may be random or block copolymers.

The cationic polymer(s) may be linear or branched and/or may be random or block copolymers.

The cationic polymer(s) may be selected from the group consisting of:

a) Linear polyethyleneimine of the formula:

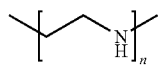

in which n is an integer representing the degree of polymerization, wherein n ranges from 50 to 20,000, alternatively from 100 to 3,500;

b) Branched polyethyleneimine consisting of primary, secondary and tertiary amine groups of the formula:

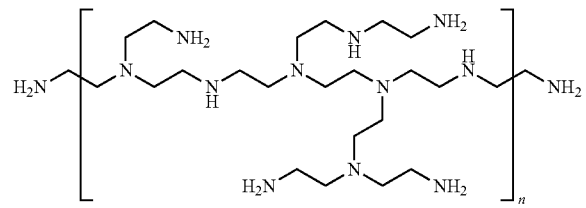

in which n is an integer representing the degree of polymerization, n ranges from 5 to 4,000, alternatively from 50 to 500;

c) Polyallylamine hydrochloride of the formula:

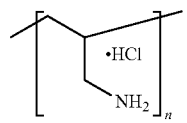

in which n is an integer representing the degree of polymerization, wherein n ranges from 50 to 20,000, alternatively from 150 to 2000;

d) Polydiallyldimethylammonium chloride of the formula:

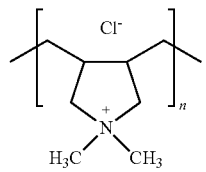

in which n is an integer representing the degree of polymerization, wherein n ranges from 10 to 20,000, alternatively from 150 to 4,000;

copolymers thereof and mixtures thereof.

The cationic polymer(s) may have a charge density at full protonation of at least 0.3, preferably at least 0.6, more preferably at least 0.8, even more preferably at least 1.0 positive charges per monomer unit.

The cationic polymer(s) may have a weight average molecular weight of more than 0.5 kDa, preferably from 0.5 kDa to 5000 kDa, more preferably from 2 kDa to 1000 kDa, even more preferably from 10 kDa to 200 kDa, most preferably from 25 kDa to 70 kDa.

Composition A, Core and Shell Alternative

As an alternative to a combination of separate cationic polymer and pigment particles in the medium and as an alternative to the pretreatment, the cationic polymer and pigment(s) may have a "core-shell structure" (core-shell morphology). In the case that the cationic polymer and pigment(s) have a "core-shell structure", the "core" corresponds to the "naked" pigment which features the same properties as defined hereinbefore with reference to the "pigment(s)". The "shell" corresponds to a coating layer surrounding the "core". The pigments having a core-shell structure may have a D50 particle diameter of from 20 nm to 1 micron, typically 60 nm to 900 nm, more typically 100 nm to 600 nm. D50, the median diameter by volume, is defined as hereinbefore. As such, the present invention also relates to a hair treatment composition comprising a core-shell pigment, wherein the core of the pigment comprises an inorganic and/or organic material, and wherein the shell of the pigment comprises at least one cationic polymer, the at least one core-shell pigment having a D50 particle diameter of 20 nm to 1 μm.

The shell surrounding the core may comprise one or more polymeric shell layers. Typically, the shell may comprise a cationic polymeric shell layer.

The cationic polymeric shell layer is typically made of one or more cationic polymer(s). Optionally, additional shell layer(s) may be positioned (arranged) on top of the first polymeric shell double layer. For instance, only one additional cationic polymeric shell layer may be positioned (arranged) on top of the anionic shell layer of the first polymeric shell double layer. As such, the shell surrounding the core may comprise more than one polymeric shell double layers, and typically, the shell may comprise one, two, three or four polymeric shell double layers.

If desired, a final cationic polymeric shell layer may be positioned (arranged) on top of the uppermost polymeric shell double layer. This may enhance the adhesion between the pigment(s) having a core-shell structure and hair fibers for the following reasons. Hair is naturally negatively charged. Therefore, the final shell layer of the coated hair which is positively charged can easily attach to the surface of the hair.

The method of applying the core and shell alternative of composition A may be accomplished by first pretreatment and then application of the composition A comprising the core and shell in a medium, or application of composition A comprising the core and shell and additional cationic polymer in a medium or foregoing the pretreatment with either of these two versions of the core and shell application.

B. Step B, Application of Composition B

Step B may comprise application of composition B comprising one or more anionic polymer(s) to the hair which is already coated with a version of composition A. The practice of step B introduces a polymeric layer of an anionic polymeric component layer, composition B, positioned on top of one of the foregoing versions of cationic polymeric layer with pigment particles, composition A. As previously mentioned, composition A is processed to substantially to essentially completely eliminate the medium of composition A before composition B is applied. Composition B may additionally include pigment particles optionally configured as core and shell or with an adherent coating as described herein, or Composition B may include such pigment particles while composition A does not include pigment particles according to embodiments described herein.

Step B is preferably carried out after step A. Step B may be carried out immediately after step A, or at least 1 hour after step A, or at least 24 hours after step A, or at least 10 days after step A, or at least one month after step A.

The composition B may be applied to at least a portion of the hair or may be applied all over the hair. The composition 13 may be applied in a single application over all the hair or may be applied step-by-step to the hair. The composition B may be applied step-by-step, for example, in case the hair is damaged. Applying the composition B in a step-by-step manner, may help to ensure that the hair is saturated with the composition B and may therefore provide a better coverage of the hair with the composition B.

B. Composition B, Anionic Polymer

Composition B comprises an anionic polymer and an aqueous medium as well as optional cross linker. Composition B can optionally also include pigment particles. Following application and elimination of the medium by air flow evaporation, elevated temperature evaporation, vacuum evaporation or a combination thereof, the anionic polymer forms a film layer on top of the already formed cationic polymer layer with pigment. The electrostatic interaction between the anionic carboxylate groups of the anionic polymer and the cationic amine groups of the cationic polymer enables ionic interpolymer and interlayer linking to provide a strongly adherent dual layer in which is embedded pigment. As mentioned above, the cationic nature of the underlying cationic layer enables ionic binding to the hair strand surfaces thereby providing favorable resistant and durability properties to the dual layer.

The anionic polymer(s) which are comprised in the composition B may be selected from the group consisting of anionic polymers and mixtures thereof. The anionic polymer embodiments may be based upon an organic polymer having carboxylic acid groups as well as other anionic groups as discussed below. The anionic polymer(s) may have a charge density at full deprotonation of at least 0.3, preferably at least 0.6, more preferably at least 0.8, even more preferably at least 1.0 negative charges per monomer unit.

As a carboxyl containing anionic polymer, the anionic polymer embodiments may be a carboxyl polymer that includes homopolymer, copolymer or terpolymer embodiments. These embodiments comprise appropriate monomeric units of olefinic carboxylic acids such as but not limited to (meth)acrylic acid, pentadienoic acid (butadienyl carboxylic acid), itaconic acid, cinnamic acid, fumaric acid, maleic acid, unsaturated fatty acids, crotonic acid, alkenoic acids of 3 to 20 carbons, similar aromatic and aliphatic unsaturated acids as well as olefinic acid esters and amides and neutral olefinic monomers. The homopolymer may include units of olefinic carboxylic acid monomers mentioned above, for example such acids as (meth)acrylic acid, maleic acid, fumaric acid, itaconic acid, crotonic acid, pentenoic acid pentadienoic acid, isoprenoic acid, partially hydrolyzed polyacrylonitile and optional olefinic acid monomer derivatives duplicative of these said olefinic carboxylic acid monomers but having at least one of the carboxylic acid groups activated with a leaving group. The homopolymer in this context has a carboxylic acid group or a leaving group acid derivative as a side chain with each monomeric unit. The copolymer and terpolymer may include units of said olefinic carboxylic acid monomers and in addition may include one or more monomeric units of esters of said olefinic carboxylic acid monomers wherein the esterifying alcohol is a linear, branched or cyclic alkyl monoalcohol or diol of 1 to 6 carbons for the linear alkyl group (2 to 6 carbons for the diol), 3 to 6 carbons for the branched alkyl group and 3 to 10 carbons for the cyclic alkyl group, amides of said olefinic carboxylic acid monomers. N-alkyl amides of said olefinic carboxylic acid monomers wherein the alkyl group is a linear, branched or cyclic alkyl group as described for the monoalcohol, N-aminoalkyl amides of said olefinic carboxylic acid monomers wherein the amidating amine is a linear, branched or cyclic alkyl diamine with 2 to 6 carbons in the linear alkyl group, 3 to 6 carbons in the branched alkyl group and 3 to 10 carbons in the cyclic alkyl group, neutral olefinic monomers including those of the formula: $HR^1C=CHR^2$ or $HR^1C=CH-CR^3=CHR^4$ wherein $R^1$, $R^2$, $R_3$ and $R^4$ are each independently selected from hydrogen, linear alkyl of 1 to 6 carbons, branched alkyl of 3 to 6 carbons, cyclic alkyl of 3 to 10 carbons, phenyl, phenyl substituted by methyl, ethyl, $CONH_2$, COOH, $-(CH_2)_nCOOH$, $NO_2$, CN, $SO_3H$, $SONH_2$, pyridyl, $O_2CR'$ wherein R' is alkyl of 1 to 3 carbons, vinyl and alkyl vinyl having 1 to 3 carbons in the alkyl group.

The carboxylic acid polymer or copolymer may also comprise a carboxylate ester polymer or copolymer which includes monomeric units of one or more olefinic carboxylate esters such as (meth)acrylates or similar olefinic esters and olefins as described above. These embodiments comprise the copolymer of one or more repeating monomeric units selected from olefinic ester monomers wherein the ester is a (meth)acrylate, maleate, butenoate, pentenoate and similar olefinic or vinyl esters and the esterifying alcohol is a linear, branched or cyclic alkyl monoalcohol or diol of 1 to 6 carbons for the linear alkyl group (2 to 6 carbons for the diol), 3 to 6 carbons for the branched alkyl group and 3 to 10 carbons for the cyclic alkyl group. Included also as possible repeating monomeric units of the copolymer are olefinic carboxamide monomers, N-alkyl carboxamide monomers wherein the alkyl group is a linear, branched or cyclic alkyl group as described for the monoalcohol, N-aminoalkyl olefinic carboxamide monomers wherein the amidating amine is a linear, branched or cyclic alkyl diamine with 2 to 6 carbons in the linear alkyl group, 3 to 6 carbons in the branched alkyl group and 3 to 10 carbons in the cyclic alkyl group. Additionally, neutral repeating olefinic monomeric units are possibilities for the copolymer. Monomers providing repeating olefinic monomeric units include those of the formula: $HR^1C=CHR^2$ wherein $R^1$ and $R^2$ are each independently selected from hydrogen, linear alkyl of 1 to 6 carbons, branched alkyl of 3 to 6 carbons, cyclic alkyl of 3 to 10 carbons, phenyl, phenyl substituted by methyl, ethyl, $CONH_2$, COOH, $NO_2$, CN, $SO_3H$, $SONH_2$, pyridyl, $O_2CR^3$ wherein $R^3$ is alkyl of 1 to 3 carbons, vinyl and alkyl vinyl having 1 to 3 carbons in the alkyl group. The molar percent amounts of the foregoing monomers making up the monomeric units of the copolymer may range up to substantially close to one hundred molar percent. The copolymer may include monomeric units of olefinic carboxylic acid monomers including (meth)acrylic acid, maleic acid, fumaric acid, itaconic acid, crotonic acid, pentadienoic acid, isoprenoic acid and/or pentenoic acid. The molar percent amounts of such olefinic carboxylic acid monomeric units of the copolymer constitutes a minor to moderate molar percent. While the acid number cannot provide an accurate molar percent for the number of olefinic carboxylic acid monomer units in this situation, the copolymer typically and essentially for each embodiment possesses an acid number indicating that a minor to moderate molar amount of the olefinic monomeric units of the copolymer is the olefinic carboxylic acid monomeric unit.

The anionic polymer(s) may have a weight average molecular weight of at least 1 kDa, preferably from 10 kDa to 1000 kDa, more preferably from 70 kDa to 500 kDa.

Additional anionic polymer embodiments may comprise one or more monomer unit(s) comprising one or more functional group(s) selected from the group consisting of sulfate, sulfonate, carboxylate, phosphate, phosphonate groups and mixtures thereof. The functional group(s) may preferably be selected from the group consisting of sulfate, sulfonate, carboxylate groups and mixtures thereof.

The anionic polymer(s) may be selected from the group consisting of polystyrene sulfonate salts, λ-carrageenan salts, dextran sulfate salts, polyacrylic acid salts, poly(meth-acrylic acid) salts, alginic acid salts, carboxymethylcellulose salts, polystyrene sulfonate/polystyrene copolymer salts, copolymers thereof and mixtures thereof. The salts may be sodium salts.

Examples of the anionic polymer(s) may be but are not limited to embodiments including:

a) Polystyrene sulfonate (PSS) sodium salt of the formula:

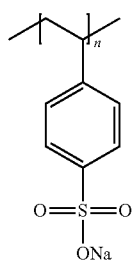

in which n is an integer representing the degree of polymerization, wherein n ranges from 50 to 20,000, alternatively from 150 to 500;

b) Co-polymer of polystyrene sulfonate (PSS) sodium salt and poly(4-styrenesulfonic acid-co-maleic acid) of the formula:

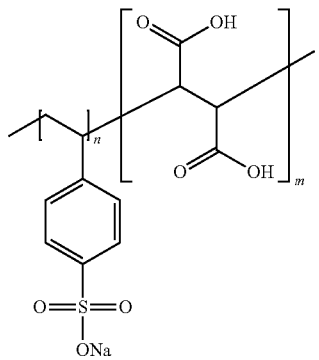

in which n and m are integers representing the degree of polymerization, wherein n+m ranges from 50 to 20,000, alternatively from 150 to 2500;

c) λ-Carrageenan;
d) Dextran sulfate sodium salt;
e) Polyacrylic acid (PAA) of the formula:

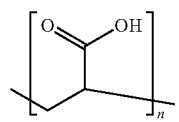

in which n is an integer representing the degree of polymerization, wherein n ranges from 50 to 20,000, alternatively from 150 to 5000;

f) Alginic acid sodium salt;
g) Carboxymethylcellulose sodium salt of the formula:

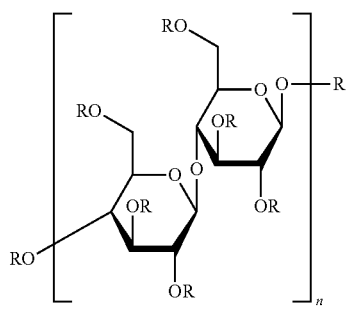

in which :R is H or $(CH_2)_2COONa$ and n is an integer representing the degree of polymerization; copolymers thereof and mixtures thereof.

These polymers and copolymer embodiment examples may be random or block copolymers.

The carboxylic acid polymer and copolymer embodiments including the (meth)acrylate copolymer embodiments generally may have an acid value ranging from about 0.1 to about 700, preferably about 1 to about 400, more preferably 10 to 190, especially more preferably 2.5 to 250, most preferably 40 to 200. The weight percentage of carboxylic acid monomer relative to the total weight of the polymer may range from about 0.2 weight percent to 30 weight percent. The molar ratio of carboxylic acid monomer to total monomer may range from 0.2:100 to 30:100, preferably 0.5:100 to 28:100, more preferably 1.0:100 to 26:100 most preferably 2:100 to 25:100. The molar ratio of 100:100 means that all monomeric units are carboxylic acid units.

Preferably, the carboxylate ester copolymer embodiments may have an acid value ranging from about 1 to about 200 preferably about 2 to 125, more preferably about 3 to 100 and most preferably about 4 to 75, or about 30. Preferably the carboxylate ester monomeric units of the copolymer can be converted to some extent to carboxylic acid groups by hydrolysis of the ester monomers during polymerization and work up. Alternatively, olefinic carboxylic acid monomer can be added to the monomeric mixture to be polymerized and the polymerization and work up processes can be conducted under conditions designed to substantially avoid ester hydrolysis.

The weight average molecular weight Mw of the carboxylic acid polymer and copolymer embodiments may range from about 300 daltons to about 10 MDa. Preferably the Mw may range from about 500 Da to about 1 MDa, more preferably about 750 Da to about 500 kDa, especially more preferably about 1 kDa to about 500 kDa, especially most preferably about 5 kDa to about 200 kDA. The polydispersity may range from about 1 to about 10, preferably about 1.1 to about 7, more preferably 1.1 to about 5, most preferably 1.1 to about 3.

The carboxylic acid and carboxylate ester polymer embodiments are all water soluble while their degree of water solubility depends upon several factors including the Mw, the molar content of carboxylic acid monomer, the pH and temperature. The water solubility of the carboxylic acid polymer embodiments can also be increased by neutralization with a base. The neutralization can be performed with any base. Particularly the base useful for neutralization includes volatile bases, for example ammonia and or volatile organic amines as discussed elsewhere in this disclosure. Volatile refers to a material with a boiling point below 200 C at standard atmospheric pressure. At lower Mw and higher molar content of carboxylic acid monomer, the carboxylic acid polymer without neutralization is water soluble at all pH increments. At higher Mw and lower molar content of carboxylic acid monomer the carboxylic acid polymer without neutralization will be water soluble to a certain moderate extent such as from 5 wt % to 15 wt % relative to the weight of polymer and water. The solubility of these embodiments of the carboxylic acid and/or ester polymer can be increased by neutralization so that the embodiments of the resulting neutralized carboxylic acid or ester polymer will be fully soluble in water. The concentrations of these embodiments of neutralized high Mw, low carboxylic acid monomer content polymers can range from a minimum of about 5 weight percent of water up to 90 weight percent of water. These weight percentages address the saturation points and depend at least in part upon the neutral olefinic monomer, carboxylic acid ester or amide monomer content, carboxylic acid monomer content and the weight average molecular weight of the polymer. At high percentage of carboxylic acid monomer content of the polymer and low Mw, the saturation point will range up to 90 weight percent or greater. At low percentage of carboxylic acid monomer content of the polymer and high Mw, the saturation point will be at the lower end of the range.

The viscosity of compositions A and B function to hold the compositions on the hair strands while the coatings are formed. The viscosity substantially avoids free translational flow of the compositions. Free translation flow would cause the compositions to rapidly run and drip off the surfaces of the hair strands. Nevertheless, the viscosity is not so high that it will not undergo self-leveling to substantially uniformly coat strands of hair. Appropriate viscosity of compositions A and B is the result of the interaction of the cationic polymer for composition A and the anionic polymer for composition B, their concentration, and as appropriate, optional viscosity control agents, optional suspending agents and optional thickening agents. Generally, the viscosity of the compositions may range from about 0.1 to about 200 Pa $s^{-1}$, preferably 1 to 100 Pa $s^{-1}$, more preferably 10 to 75 Pa $s^{-1}$. Viscosity measurements are carried out on a controlled stress rheometer eg. Using an AR2000 type manufactured by TA Instruments, or equivalent instrument. A 6 cm flat acrylic cross hatched parallel plate geometry (TA item 518600.901) and a stainless steel cross hatched base plate (TA item 570011.001) are used. The rheometer is prepared for flow measurements as per standard manufacturer procedure. The parallel plate geometry gap is set to 1000 microns. The flow procedure is programmed to the rheometer with the following conditions: continuous stress ramp 0.1-300 Pa over 2 minutes at 25° C., including 250 measurement points in linear mode. The product is loaded into the geometry as per standard procedure and the measurement commences at 5 min after the mixture preparation. Shear stress value at 10 $sec^{-1}$ shear rate is obtained from the shear stress vs. shear rate curve, and the corresponding viscosity is calculated by dividing the obtained shear stress by 10.

For the cross linking embodiment of composition B, the carboxylic acid and/or carboxylate ester polymer can become cross linked in situ upon the application of the cross linkable composition B to the hair already coated with composition A. The cross linking may be covalent, non-covalent, hydrogen bonding, electrostatic interaction, ionic interaction or any combination thereof. Covalent crosslinking may be facilitated by inclusion of a minor to moderate amount of cross linker relative to the number of carboxylic acid groups per polymer molecule. Embodiments of the cross linker include but are not limited to polyol, polyamine, polycarbodiimide, polyisocyanate or multivalent metal complex, examples of which include but are not limited to diol, triol, diamine, triamine, his or tris (alkylcarbodimidoalkylenyl), alkyl diisocyanate or 3-alkylenylalkyltriisocyanate, zinc or zirconium complexes including but not limited to specific examples such as N,N'-diethyl tri(ethylenyl carbodiimide), di-cyclohexylisocyanate alkylene glycol or diamine of 2 to 6 carbons in the alkylene group. The cross linking agent can combine with carboxylic acid groups of adjacent polymers to form diester, triester, diamide, triamide, diurea, triurea, diurethane triurethane links. Similarly, the diol ester or aminoalkyl amide of a few of the carboxylic acid groups of the polymer can be present and will combine with carboxylic acid groups of adjacent polymer molecules to form diester or diamide links. Alternatively, a few carboxylic acid derivatives with a facile leaving group can be included in the polymer. The derivative will combine with a carboxylic acid group of an adjacent polymer so as to form an anhydride link. With all cross linking agents, whether separate or internal, cross linking such as in a range of 0.1 percent to 99 percent and all individual percentages within this range, preferably about 1 percent to about 75 percent, more preferably about 2 percent to about 55 percent, especially more preferably about 4 percent to 40 percent, most preferably about 5 percent to about 25 to about 30 percent, and all individual percentages within each of these ranges, relative to the available carboxylic acid groups of the polymer will achieve appropriate three dimensional cross linked polymers having a net and/or a star configuration. The molar ratio of cross linker to carboxylic acid polymer will depend upon the ratio of carboxylic acid monomeric units to total units of the polymer as described above and the degree of cross linking desired or needed to achieve the following properties of the cross linked polymer. Routine experimental methods can be used to determine the combination or ratios needed to provide significant wash resistance and free flowing hair qualities. The in situ cross linking will improve resistance of the coating toward removal with dilute soap or shampoo aqueous solutions and will provide appropriate adherent ability to the hair strands while preserving free hair flow properties and avoid stickiness and clumping.

The concentration of the anionic polymer such as a carboxylic acid polymer or copolymer or carboxylate ester copolymer in the composition may range from about 2% to about 30%, preferably about 4% to about 25%, more preferably about 6% to about 20%, most preferably about 8% to about 15% by weight relative to the total weight of the composition. Specific concentrations include about 2%, about 4%, about 6%, about 8%, about 10%, about 12%, about 14%, about 16%, about 18%, about 20%, about 22% about 24% by weight relative to the total weight of the composition. The determination of the concentration for embodiments of the anionic polymer such as the carboxylic acid polymer will depend in part upon the resulting viscosity, the saturation point of the anionic groups, the carboxylic acid groups and/or ester polymer in the medium and the interaction, if any, between the anionic groups, the carboxylic acid groups or ester polymer and other components of the composition including but not limited to the cationic polymer of the already formed layer of composition A and associated material, if any. As discussed above, the viscosity is managed so that the composition will not run off the surfaces of strands of hair yet will level and flow to substantially coat those surfaces. Development of appropriate viscosity in part by management of the concentration of the anionic polymer can be experimentally determined by routine methods such as formulation of several samples of differing concentrations of polymer in the composition, coating those samples on a hair swatch and observing the flow, spread and leveling of the composition on the hair strands.

The dual component hair coloring composition can be applied to a hair strand using the coloring procedure described herein afterwards. The top of the hair strand, where it is glued together is clamped in a stand such that the hair is aligned vertically downwards. After a 5 minute dwell time it is observed if any and how much product has dripped from the hair tress. The results obtained from the several samples can be plotted against flow time and leveling time to determine an appropriate concentration or range of concentrations of the particular carboxylic acid polymer in the composition. A preferred concentration of the carboxylic acid polymer in the composition ranges from about 5% to about 45%, more preferably about 8% to about 35% and most preferably about 10% to about 30% by weight relative to the total weight of the composition. Examples of the carboxylic acid polymer concentration can be in the approximate range of 15%, 20% or 25% by weight relative to the total weight of the composition. Further examples of the carboxylic acid polymer concentration range from 0.1% to 40% by weight, such as from 0.1% to 30% by weight, for example ranging from 0.5% to 20% by weight, such as from 1% to 20% by weight, for example ranging from 10% to 15% by weight, relative to the total weight of the hair coloring composition.

The anionic polymer may be neutralized with a volatile base as described above so that it is completely water soluble. At the foregoing Mw's the un-neutralized poly (meth)acrylic acid will be soluble in water but the concentration of the un-neutralized polymer will not be as high as that of the neutralized polymer.

The carboxylate ester copolymer may also be formulated and exemplified as a copolymer of a minor amount of carboxylic acid along with carboxylate esters and olefins and a few of the carboxylic groups may be converted to acyl groups bonded to leaving groups that will enable the acyl groups to form anhydrides with carboxylic acid groups. Appropriate leaving groups include imidazolonyl moieties, carbodiimide moieties, t-butyl anhydride moieties and activated ester moieties, Upon formulation of this copolymer into the medium, the acyl-leaving groups will combine with carboxylic acid groups to form cross link anhydride groups. The number of anhydride groups relative to the total number of carboxyl groups of the copolymer is moderate to significant such as the ratios provided above.

The carboxylic acid polymer, copolymer and carboxylate ester polymer may also be formulated and exemplified as a homopolymer of olefinic carboxylic acid alone and a few of the carboxylic groups may be converted to acyl groups bonded to leaving groups that will enable the acyl groups to form anhydrides with carboxylic acid groups. Appropriate leaving groups include imidazolonyl moieties, carbodiimide moieties, t-butyl anhydride moieties and activated ester moieties. Upon formulation of this homopolymer into the medium just before addition to the hair, the acyl-leaving groups will combine with carboxylic acid groups to form cross link anhydride groups. The number of anhydride groups relative to the total number of carboxyl groups of the homopolymer can be small, such as 1% to 5%, preferably 2% to 3% so that this kind of crosslinking would be low relative to the primary in situ cross linking described above. This kind of cross linking enables removability of the cross linked polymer as a coating on the hair strands yet provides resistance toward aqueous penetration into the polymer lattice when the polymer is in a solidified state.

The carboxylic acid polymer may also be formulated and exemplified as a copolymer or terpolymer of olefinic carboxylic acid and a neutral olefin monomer selected from the group consisting of olefinic carboxylate ester wherein the esterifying alcohol is a C1 to C22 monoalcohol, preferably methanol, ethanol, propanol, isopropanol or n-butanol, (meth)acrylamide, styrene, carboxystyrene (i.e. vinylbenzoic acid), carboxyamidostyrene (i.e. vinylbenzamide), vinylpyridine, vinyl oxyalkanoyl (vinyl acetate and homologs of the acetate) and any combination thereof. Preferred olefin monomers include methyl (meth)acrylate, (meth)acrylamide and styrene. Of these preferred olefin monomers, methyl acrylate, acrylamide and styrene are preferred. More preferred olefin monomers are methyl acrylate and acrylamide with methyl acrylate being most preferred. The copolymer may include one or more neutral olefin monomers and preferably only one while the terpolymer may include two or more neutral olefin monomers and preferably two or three. The molar percent of the (meth) acrylic acid monomer relative to the total moles of monomer of the copolymer or terpolymer may range from about 30 mole percent to about 0.2 mole percent, preferably about 28 mole percent to about 0.5 mole percent, more preferably 26 mole percent to about 1 mole percent, most preferably about 25 mole percent to about 2 mole percent. The remaining mole percent is made up of one or more of the neutral olefin monomers. Its Mw and polydispersity may range as described above.

The copolymer or terpolymer is neutralized with a volatile base as described above so that it is completely water soluble. At the foregoing Mw's the un-neutralized copolymer or terpolymer will display some solubility in water but the concentration of the un-neutralized polymer will not be as high as that of the neutralized polymer.

The olefinic carboxylate ester copolymer may also be formulated and exemplified as a copolymer of a neutral monomer selected from the group consisting of olefinic carboxylate ester such as (meth)acrylate ester or pentadienoate ester wherein the esterifying alcohol is a C1 to C22 monoalcohol, preferably methanol, ethanol, propanol, iso-propanol or n-butanol, (meth)acrylamide, styrene, carboxystyrene (i.e. vinylbenzoic acid), carboxyamidostyrene (i.e. vinylbenzamide), vinylpyridine, vinyl oxyalkanoyl (vinyl acetate and homologs of the acetate) and any combination thereof. Preferred olefin monomers include methyl (meth) acrylate, (meth)acrylamide and styrene. Of these preferred monomers, methyl acrylate, acrylamide and styrene are preferred. More preferred monomers are methyl, ethyl, propyl, butyl, pentyl, hexyl, ethyl hexyl and lauryl acrylate, styrene and acrylamide. Most preferred is a copolymer produced from the monomers styrene, acrylic acid and one or more acrylate esters with methyl, ethyl, propyl, butyl and lauryl groups. The acid function of the copolymer can be achieved and controlled by partial basic hydrolysis of the carboxylate ester under controlled conditions during the polymer formation. Alternatively, a minor amount of olefinic carboxylic acid monomer can be added to the monomer mixture to be polymerized. Following work-up of copolymer isolation, the copolymer may be titrated with a volatile base as described above to neutralize the acid groups present so as to increase solubility and/or dispersibility in the medium.

The copolymer and terpolymer may be constructed with random distribution of the different monomer units along the polymer backbone or may be block copolymers which has blocks of single monomer units or may be a graft copolymer which has one monomer unit forming the polymer backbone and a different monomer unit forming polymeric side chains. The different constructions of polymer provide differing polymer to polymer binding properties and different macromolecular characteristics. The block copolymer can provide regions of hard and soft polymer characteristics. A block copolymer can display crystalline regions and amorphous regions that can enable development of water soluble and water resistant regions. Blocks of differing electronic and lipophilic character can impart an open repulsive character to the polymer so that tightly fit inter-structures are minimized. A grafted polymer or segmented polymer are capable of intertwined conformation and compact molecular dimension so as to enable tightly fitted inter-structures.

The homopolymer, copolymer and terpolymer may also be constructed to include reactive side chains having terminal hydroxyl or amine groups. These are described above as monomeric carboxylate esters of diols and carboxyamides of diamines. The pendant hydroxyl or amine groups of these monomeric units of the polymer can combine with the carboxyl groups of the carboxylic acid monomeric units of another polymer to provide in situ cross-linking. To provide the combination, the water bi-product of the cross-linking can be removed by evaporation during application to drive the thermodynamic equilibrium to completion. In the context of the present invention, this thermodynamic shift can occur during the setting of the hair coloring composition on the strands of hair. The extent of cross-linking may be controlled so that the mechanical and chemical properties of the cross linked polymer as described herein are preserved. These properties include ability to adhere to hair strands, ability to maintain flexibility and free flowing character of the hair, ability to provide remanence, avoidance of stickiness and avoidance of clumping.

The glass transition temperature of the anionic polymer in part contributes to the flexibility, strength, hardness and similar qualities of the coating on the keratin fiber surfaces. The glass transition temperature of the polymer embodiments may range in degrees Celsius from about −60° C. to about 90° C., preferably about −50° C. to about 20° C. This glass transition temperature or $T_g$ determines the solid-solid transition of the polymer from a hard glassy material to a soft rubbery material. If the $T_g$ of the polymer is too high, the coating on the keratin fibers will be stiff and inflexible. This is an undesirable result. The coating should be soft, flexible and unnoticeable to touch and sight yet should not flake, break-up or otherwise release from the keratin fiber, and especially from human hair, when stroked by a hand or brushed with a brush. The Tg of a polymer can be measured using ASTM D7426-08.

Examples of the carboxylic acid polymer of the hair coloring composition according to the present invention include Ultrahold Strong® sold by BASF, Luvimer® sold by BASF, Amerhold® sold by Amerchol, Acudyne® Rohm & Haas, and Acrylidone® sold by ISP. All of these commercial polymers contain monomeric units of (meth)acrylic acid and are copolymers containing (meth)acrylate esters, amides and/or neutral olefins.

Other Examples

Acrysol ASE-75 Thickener (Dow), Primal 3208 Emulsion (Dow), Acrysol ASE-95NP Thickner (Dow), Acrysol I-62A (Dow), Acrysol WS-24 Colloidal (Dow), Acrysol WS-50 Colloidal Dispersion (Dow), Plexisol P 550-40 (Kremer), Pemulen TR-1 Polymer (Lubrizol), Pemulen TR-2 Polymer (Lubrizol), FIXATE FREESTYLE POLYMER (Lubrizol), Rovene 6005 (Mallard Creek), Rovene 6017 (Mallard Creek), Rovene 6020 (Mallard Creek), Rovene 6103 (Mallard Creek), Rovene 9410 (Mallard Creek), Silform HYFLEX (Motnentive), Mowinyl 6718 (Mowinyl), Mowinyl 6750 (Mowinyl), Mowinyl 67510 (Mowinyl), Mowinyl 6760 (Mowinyl), Mowinyl 6960 (Mowinyl), X-200 (PMC/SEIKO), J-140A (PMC/SEIKO), RE-1075 (PMC/SEIKO), COVACRYL P12 (Sensient Covacyl E14 WP (Sensient), COVACRYL MT10 (Sensient), WorleeMicromer C20/42 (Worlee), WorleeMicromer C60/42 (Worlee), WorleeMicromer C60/42 NP (Worlee), Avalure AC 120 Polymer Lubrizol). Excluded are Neocryl 1125 and 1127.

B. Plasticizer

If the glass transition temperature of the polymer is too high for the desired use yet the other properties of the polymer are appropriate, such as but not limited to color and wash fastness, one or more plasticizers can be combined with the hair coloring composition embodiments so as to lower the $T_g$ of the carboxylic acid polymer and provide the appropriate feel and visual properties to the coating. The plasticizer can be incorporated directly in the coloring composition or can be applied to the hair before or after the coloring composition. The plasticizer can be chosen from the plasticizers usually used in the field of application.

The plasticizer or plasticizers can have a molecular mass of less than or equal to 5,000 g/mol, such as less than or equal to 2,000 g/mol, for example less than or equal to 1,000 g/mol, such as less than or equal to 900 g/mol. In at least one embodiment, the plasticizer, for example, has a molecular mass of greater than or equal to 40 g/mol.

Thus, the hair coloring composition can also comprise at least one plasticizer. For example, non-limiting mention can be made, alone or as a mixture, of common plasticizers such as: glycols and derivatives thereof, silicones, silicone polyethers, polyesterpolyols; adipic acid esters (such as diisodecyladipate), trimellitic acid esters, sebacic acid esters, azalaeic acid esters; nonlimiting examples of glycol derivatives are diethylene glycol ethyl ether, diethylene glycol methyl ether, di ethylene glycol butyl ether or di ethylene glycol hexyl ether, ethylene glycol ethyl ether, ethylene glycol butyl ether, or ethylene glycol hexyl ether; polyethylene glycols, polypropylene glycols, polyethylene glycol-polypropylene glycol copolymers, and mixtures thereof, such as high molecular weight polypropylene glycols, for example having a molecular mass ranging from 500 to 15,000, for instance glycol esters; propylene glycol derivatives such as propylene glycol phenyl ether, propylene glycol diacetate, dipropylene glycol ethyl ether, tripropylene glycol methyl ether, diethylene glycol methyl ether, and di propylene glycol butyl ether. Such compounds are sold by Dow Chemical under the names DOWANOL PPH and DOWANOL DPnB; acid esters, for example esters of carboxylic acids, such as triacids, citrates, phthalates, adipates, carbonates, tartrates, phosphates, and sebacates; esters derived from the reaction of a monocarboxylic acid of formula $R_{11}COOH$ with a diol of formula $HOR_{12}OH$ in which R11 and $R_{12}$, which can be identical or different, are chosen from a linear, branched or cyclic, saturated, or unsaturated hydrocarbon-based chain containing, for example, from 3 to 15 carbon atoms for example the monoesters resulting from the reaction of isobutyric acid and octanediol such as 2,2,4-trimethyl-1,3-pentanediol, such as the product sold under the reference TEXANOL ESTER ALCOHOL by the company Eastman Chemical; oxyethylenated derivatives, such as oxyethylenated oils, such as plant oils, such as castor oil; mixtures thereof.

Among the esters of tricarboxylic acids mention can be made of the esters of triacids wherein the triacid corresponds to formula

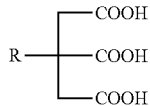

wherein R is a group —H, —OH or —OCOR' wherein R' is an alkyl group containing from 1 to 6 carbon atoms. For example, R can be a group —OCOCH$_3$. The esterifying alcohol for such tricarboxylic acids may be those described above for the monocarboxylic acid esters.

The plasticizer can be present in the composition of the present disclosure in an amount from about 0.01% to 20%.

C. Medium

The medium of the hair coloring composition embodiments of the invention may be water alone, water in mixture with a volatile polar protic or aprotic organic solvent, or a non-aqueous solvent or a mixture of non-aqueous solvents with polar protic or aprotic polar organic solvent. In general, the medium is any solvent suitable for dissolving the carboxylic acid polymer of the embodiments of the hair coloring composition described herein. In addition to water present in the medium, a volatile solvent may be present including a volatile polar protic or aprotic organic solvent, or mixtures thereof. Volatile organic solvents of which non-limiting mention may be made include: volatile pyrolidones 1-methylpyrrolidin-2-one, volatile $C_1$-$C_4$ alkanols such as methanol, ethanol or isopropanol; esters of liquid $C_2C_6$ acids and of volatile $C_1$-$C_8$ alcohols such as methyl acetate, n-butyl acetate, ethyl acetate, propyl acetate, isopentyl acetate, or ethyl 3-ethoxypropionate; ketones that are liquid at room temperature and volatile, such as methyl ethyl ketone, methyl isobutyl ketone, diisobutyl ketone, isophorone, cyclohexanone, or acetone; volatile polyols such as ethylene glycol and propylene glycol.

According to at least one embodiment of the present disclosure, the organic solvent is chosen from ethanol, isopropanol, acetone, and isododecane.

The medium with or without one or more volatile organic solvent may be present in the composition according to the present disclosure in an amount ranging from about 0.1% to about 95% by weight, such as from about 1% to about 70% by weight, for example ranging from 5% to 90% by weight relative to the total weight of the composition.

The ratio of solvent to the pigment microparticles comprising at least one pigment can be between about 1:5 to about 10:1, about 1:2 to about 8:1 or about 7:1 to about 2:1.

According to an embodiment, the medium is an aqueous medium.

D. Pigments

The hair coloring composition embodiments of the present invention make it possible to obtain colored and remanent coatings, without substantially altering the keratin fibers. In one embodiment, the hair coloring composition embodiments of the present invention have a coverage index of 15 or greater, preferably 20 or greater, more preferably 30 or greater or most preferably 60 or greater. In some examples, the hair coloring composition embodiments of the present invention have a coverage index of 15 to 70, 15 to 60, 30 to 60 or 50 to 70.

The coverage index of the hair coloring composition embodiments of the present invention is determined by preparing a hair coloring composition comprising 1% total pigment (e.g., at least one organic pigment) by weight and is applied to a BYK chart 2855 uncoated drawdown card using a BYK bar film applicator (5561-Single Bar 6", 0.5 mils). A series of draw cards are used side by side to ensure that the bar film applicator can be used to get the target film thickness. When the hair coloring composition has dried, 24 hours in a 40° C. oven, the color of the resulting color is measured on the white and black sections of the BYK chart using a Minolta spectrophotometer CM-2600d. The L*a*b values are calculated with D65 lighting on the two sections are then used to compute the coverage index, which is the difference in color between the applied color on the black and white sections of the drawdown card as follows:

Coverage Index=$((L_{black}-L_{white})^2+(a_{black}-a_{white})+(b_{black}-b_{white})^2)^{0.5}$.

The hair coloring composition embodiments of the present invention can also have a color gamut of great than 250, greater than 500, greater than 750, greater than 1000, greater than 1250, greater than 1500 or greater than 2000.

The color gamut is determined by adding the pigment to be tested the hair coloring composition, and tested at a level such that when applied to hair, the resulting lightness or L* value of the hair is 60±2. Two hair tresses (Kerling, Natural White special quality) have the hair coloring composition applied and brushed into the hair within a plastic weigh boat at level of 1 g per g of hair. The hair is then dried using a hairdrier while being combed to produce two tresses with individualized hair strands. A Minolta spectrophotometer CM-2600d is used to measure the color of the tresses, on both the front and back sides, and the values are averaged. The D65 L*a*b values are calculated. When the three pigments have each been measured within the target L* values of 60±2 the color gamut can be calculated. First the lengths of each side of the resulting triangle in the a*b plane are computed using the expression:

$$\text{Side Length} = ((a_{pigment\ 1} - a_{pigment\ 2})^2 + (b_{pigment\ 1} - b_{pigment\ 2})^2)^{0.5}.$$

The resulting color gamut is calculated using the expression:

$$\text{Color Gamut} = (S(S-x)(S-y)(S-z))^{0.5}$$

wherein x, y and z are the three length of the side of the triangle within the a*b plane, and $S=(x+y+z)/2$. Where more than three pigments are used, this calculation can be performed for each combination of the three pigment from the more than three pigments used, and the largest Color Gamut is selected.

As used herein, the term "pigment" generally refers to any particle colorant having or containing pigment material that gives hair fibers color including black and white, such as titanium dioxide that give only white to hair fibers. The pigments are substantially water-insoluble. The pigments, to distinguish from dyes presented in molecular from, are also referred to as pigment microparticles or pigment particles. The pigments can be organic, inorganic, or a combination of both.

The at least one pigment that can be used can be chosen from the organic and/or mineral pigments known in the art, such as those described in Kirk-Othmer's Encyclopaedia of Chemical Technology and in Ullmann's Encyclopaedia of industrial Chemistry. The pigments comprised in the microparticles comprising at least one pigment will not substantially diffuse or dissolve into keratin fibers. Instead, the pigment comprised in the microparticles comprising at least one pigment will substantially remain separate from, but attached to the keratin fibers.

The at least one pigment can be in the form of powder or of pigmentary paste. It can be coated or uncoated. The at least one pigment can be chosen, for example, from mineral pigments, organic pigments, lakes, pigments with special effects such as nacres or glitter flakes, and mixtures thereof. The at least one pigment can be a mineral pigment. As used herein, the term "mineral pigment" generally means any pigment that satisfies the definition in Ullmann's encyclopedia in the chapter on inorganic pigments. The mineral pigments that can be useful in the present disclosure include iron oxides, chromium oxides, manganese violet, ultramarine blue, chromium hydrate, and ferric blue.

Pigment Shape

The pigment microparticles can have any suitable shape, including substantially spherical. But the pigment microparticles can also be oval, elliptical, tubular, irregular, etc., or even combinations of various shapes. In addition, the pigment microparticles can have two dimensions, length and width/diameter, of similar magnitude. In addition, the pigment microparticles can be platelets, i.e. having a thickness that is substantially smaller than the planar dimension. For example five, ten or even 20 times smaller in thickness than in the planer dimension. The pigments can be surface treated, surface coated or encapsulated.

In a particular aspect, the pigment microparticles can have a shape approximating that of a sphere, in which case the microparticles are referred to as being microspheres. Pigment microparticles which can be described as microspheres are understood as particles having an aspect ratio, defined as a function of the largest diameter, or largest dimension, dmax and the smallest diameter, or smallest dimension, drain, which can be orthogonal to each other: AR=dmax/dmin which is from about 1:1 to 10:1, preferably from 1:1 to 5:1, more preferably from 1:1 to 4:1, such as from 1:1 to 3:1. More particularly, the expression "spherical-type" means that the pigment microparticles have a shape approximating that of a sphere. In other words, the pigment microparticles can be nearly orbicular in shape and can have a cross-sectional geometry that is essentially circular. Although not excluded, this does not necessarily mean that the pigment microparticles have the shape of a perfect sphere or ball. More likely, the shape of the pigment microparticles can exhibit a certain deviation from a sphere as long as the skilled person considers the shape as being similar to a sphere or as an approximation of a sphere.

In addition, the pigment microparticles can have a rather two dimensional shape, with the smallest dimension substantially smaller than the two other dimensions, in which case the microparticles are referred to as being 2-dimensional microparticles (e.g., particles having flake morphology). For example, the thickness of the microparticles can be significantly less than their length and width. The length and width can be of similar magnitude. Examples includes pigment microparticles having a shape of platelets, i.e. with a thickness that is substantially smaller than the planar dimension. For example, the aspect ratio AR=dmax/dmin, as defined above, of microparticles having a substantially two-dimensional shape, can be from about 10:1 to about 1000:1, preferably from about 10:1 to about 800:1, preferably from about 20:1 to about 800:1, preferably from about 10:1 to about 600:1, preferably from about 20:1 to about 600:1. Typically, the 2D-microparticles have a largest and a smallest dimension in their planer dimension, which both are significantly larger than the smallest dimension of the 2D-microparticles extending perpendicular to the planer dimension.

According to an embodiment, the pigments can include pigment microparticles of different shape. For example, microparticles of different size can be used to provide different reflecting and absorbing properties. Microparticles having different shape can also be formed of different pigment material. Furthermore, microparticles having different shape can also formed of different pigment material to provide different color.

Pigment Size

The pigments can be present in the composition in undissolved form. Depending on the shape, the pigments can have a D50[vol] particle diameter of from 0.001 micron to 1 micron.

For example, pigments that can be described as being microspheres can have a D50[vol] particle diameter of from 0.01 micron to 1 micron, preferably of from 0.015 micron to 0.75 micron, more preferably of from 0.02 micron to 0.50 micron. For example, the pigments can have a D50[vol] particle diameter of from 0.005 micron to 0.300 micron, from 0.005 micron to 0.250 micron, from 0.005 micron to 0.100 micron, from 0.005 micron to 0.250 micron, preferably 0.005 micron to 0.100 micron, preferably 0.05 micron to 0.150 micron, more preferably 0.075 micron to 0.200 micron. The microspheres can also have a D50[vol] particle diameter of from 0.6 micron to 0.9 micron, preferably of from 0.08 micron to 0.9 micron, and more preferably between of from 0.08 micron to 0.9 micron, such as from 0.08 micron to 0.8 micron, or such as of from 0.8 micron to 0.6 micron. According to an embodiment, the microspheres can also have a D50[vol] particle diameter of from 0.1 micron to 1 micron, preferably of from 0.12 micron to 1 micron, and more preferably between of from 0.16 micron to 1 micron, such as of from 0.2 micron to 1 micron, or such as of from 0.2 micron to 0.9 micron. The terms "micron" and "microns" describe the size in micrometers [µm].

In further embodiments, which can be combined with other embodiments described herein, the pigments, which can be described as microspheres, can have a D90[vol] particle diameter of from 0.1 micron to 1 micron, preferably of from 0.2 micron to 1 micron, and more preferably between of from 0.3 micron to 1 micron, such as of from 0.3 micron to 0.9 micron, or such as of from 0.4 micron to 0.8 micron, or such as of from 0.5 micron to 0.9 micron. For example, the pigments can have a D90[vol] particle diameter of from 0.005 micron to 0.300 micron, from 0.005 micron to 0.250 micron, from 0.005 micron to 0.100 micron, from 0.005 micron to 0.250 micron, preferably 0.005 micron to 0.100 micron, preferably 0.05 micron to 0.150 micron, more preferably 0.075 micron to 0.200 micron.

In some embodiments described herein, the pigments, which can be described as microspheres, can have a D10[vol] particle diameter of from 0.02 micron to 0.3 micron, preferably of from 0.06 micron to 0.3 micron, more preferably of from 0.08 micron to 0.3 micron, such as of from 0.08 micron to 0.2 micron, or such as of from 0.1 micron to 0.2 micron, or such as 0.12 micron to 0.3 micron.

In embodiments described herein, the D10[vol] particle diameter can be of from 0.02 micron to 0.3 micron and the D90[vol] can be of from 0.3 micron to 1 micron. In further embodiments, the D10[vol] particle diameter can be of from 0.06 micron to 0.2 micron and the D90[vol] can be of from 0.4 micron to 1 micron.

The particle diameter is represented by D10, D50 and/or by D90, which is the median diameter by volume. D10, D50 and D90 is measured with a Malvern Mastersizer 2000, which is a laser diffraction particle sizer and it is measured according to ISO 13320:2009(en) with Hydro 2000G or Hydro 2000S where the dispersant is water or ethanol. Detection range is from 0.01 micron to 2000 micron. 1)50 is expressed as x50 in ISO 13320:2009(en).

The term "D10," as used herein refers, to the 10th percentile number- or volume-based median particle diameter, which is the diameter below which 10% by number or volume of the particle population is found. The term "D50," as used herein refers, to the 50th percentile number- or volume-based median particle diameter, which is the diameter below which 50% by number or volume of the particle population is found. The term "D90," as used herein refers, to the 90th percentile number- or volume-based median particle diameter, which is the diameter below which 90% by number or volume of the particle population is found. The number or volume measurement is indicated by [num] for number or [vol] for volume. If not indicated otherwise, the particle size is given as D10[vol], D50[vol], and D90[vol], respectively.

Laser diffraction measures particle size distributions by measuring the angular variation in intensity of light scattered as a laser beam passes through a dispersed particulate sample analyzer and the particle size is reported as a volume equivalent sphere diameter. A discussion of calculating D50 is provided in Barber et al, Pharmaceutical Development and Technology, 3(2), 153-161 (1998), which is incorporated herein by reference. Pigment microparticles having a D50[vol] particle diameter of less than 20 nm may enter the cuticles and are therefore difficult to remove. For scattering purposes, Pigment(s) having a D10[vol] particle diameter of at least 60 nm, or at least 80 nm can be used. Pigment(s) having a D50[vol] particle diameter of more than 1 micron typically do not sufficiently adhere onto hair fibers.

According to an embodiment, the particle size distribution, either relative to the number or volume of the microparticles, of the pigment microparticles can be at least bi-modal. A bi-modal particle size distribution has two distinct peaks which are spaced relative from, while tri-modal particle size distribution has three distinct peaks. The term "peak" means a local maximum of the distribution curve. The "distance" between two peaks, expressed relative to the particle size, can be at least 0.05 micron, preferably at least 0.1 micron, such as at least 0.2 micron. Providing an at least bi-modal particle size distribution allows to tailor the optical appearance of the colored hair. For example, the scattering properties varies with the particle size so that microparticles of different size scatter the light into different directions.

The at least bi-modal particle size distribution can be relative to pigment microparticles formed by the same pigment material. In addition to that or alternatively, the at least bi-model particle size distribution can be provided by pigment microparticles of different pigment material.

The size of pigment microparticles which can be described to have a 2-dimensional shape and which are referred to as 2-dimensional microparticles can be determined by SEM. The size of 2-dimensional microparticles can also be determined by laser diffraction measurements. The particle size determined by laser diffraction is a mean size of the different dimensions of the 2-dimensional particles. The apparent D50[vol] particle diameter of 2-dimensional microparticles, as measured by SEM, can be from 0.5 micron to 50 micron, more preferably from 0.8 micron to 20 micron, more preferably from 1 micron to 15 micron, more preferably from 1.5 micron to 10 micron.

According to an embodiment, pigment microparticles are referred to as being microspheres can be used light-scattering and/or light absorbing purposes. Those particles, due to their pigment material, impart the hair with a specific color. According to an embodiment, the pigment microparticles can have a molar extinction coefficient measured at a pigment's/microparticle's $\lambda_{max}$, greater than $1.0 \times 10^4$ $M^{-1}$ $cm^{-1}$, greater than $2.0 \times 110^4$ $M^{-1}$ $cm^{-1}$, greater than $3.0 \times 10^4$ $M^{-1}$ $cm^{-1}$, greater than $4.0 \times 10^4$ $M^{-1}$ $cm^{-1}$, greater than $6.0 \times 10^4$ $M^{-1}$ $cm^{-1}$, or greater than $8.0 \times 10^4$ $M^{-1}$ $cm^{-1}$ (e.g., from about $4.5 \times 10^4$ $M^{-1}$ $cm^{-1}$ to about $7.5 \times 10^4$ $M^{-1}$ $cm^{-1}$; about $5.0 \times 10^4$ $M^{-1}$ $cm^{-1}$ to about $8.0 \times 10^4$ $M^{-1}$ $cm^{-1}$; about $5.5 \times 10^4$ $M^{-1}$ $cm^{-1}$ to about $7.5 \times 10^4$ $M^{-1}$ $cm^{-1}$; or about $6.0 \times 10^4$ $M^{-1}$ $cm^{-1}$ to about $8.0 \times 10^4$ $M^{-1}$ $cm^{-1}$).

According to an embodiment, pigment microparticles are referred to as being 2-dimensional microparticles can be mainly used for light-reflecting and/or light absorbing purposes. Those particles, due to their pigment material, mainly reflect the light without significantly alter the color of the light.

The pigment microparticles can be light absorbing, but which for wavelengths of visible light provide negligible to low or no scattering. While not wishing to bound by any specific theory, it is believed that such pigments can provide more chromatic colors. Such pigment microparticles can have a D50[vol] value between about 0.001 micron and about 0.15 micron, between about 0.005 micron and about 0.1 micron or between about 0.010 micron and about 0.075 micron.

The pigment microparticles can be predominantly light scattering for wavelengths of visible light and provide low light absorption. While not wishing to bound by any specific theory, it is believed that such pigments can provide the visual effect of lightening the hair, without the need for bleaching with ammonia or monoethanolamine and hydrogen peroxide. Such pigment microparticles, which can be microspheres, can have a D50[vol] value between about 0.05 micron to about 1 micron, between 0.08 micron to about 0.9 micron, between about 0.05 micron and about 0.75 micron, between about 0.1 micron and about 0.5 micron or about 0.15 micron and about 0.4 micron. Such materials can have a refractive index above 1.5, above 1.7 or above 2.0.

Pigments made from metal like materials which can conduct electricity, and which can absorb light and re-emit the light out of the metal to give the appearance of strong reflectance. While not wishing to be bound by any specific theory, it is believed that the absorbed light will induce alternating electric currents on the metal surface, and that this currents immediately re-emit light out of the metal. Such pigment microparticles can be platelets, e.g., having a thickness that is substantially smaller than the planar dimension. For example about five, about 10 or even about 20 times smaller in thickness than in the planer. Such platelets can have a planar dimension less than about 50 micron, such as less than 15 microns, but with a thickness less than about 1 micron, more preferably with a planer dimension less than about 12 micron, but with a thickness less than about 0.75 micron or with a plan dimension less than about 10 micron and a thickness less than about 0.5 micron.

Composite Microparticles, Combination of Microparticles, Mixtures of Microparticles The pigment microparticles can be a composite formed by two different types of pigment microparticles. Examples include a composite of a 2-dimensional microparticle and at least one microspherical particle (microsphere), a composite of different microspherical particles, and a composite of different 2-dimensional particles. Composite particles formed by 2-dimensional microparticles to which microspherical particles adhere provide an attractive alternative to a pure mixture of 2-dimensional microparticles and microspherical particles. For example, a metallic 2-dimensional microparticle can carry one or more microspherical particle such as one or more organic microspherical particle. The microspherical particles attached or bonded to the 2-dimensional microparticle can be formed of the same pigment material or can be formed of different pigment material. Composite microparticles formed of 2-dimensional microparticles and microspherical particles can provide multiple functionality in one particle such as (metallic) reflectance and dielectric scattering, reflectance and absorption.

Pigment microparticles can be composite material comprising a core of pigments made from metal like materials which can conduct electricity, and which can absorb light and re-emit the light out of the metal to give the appearance of strong reflectance. While not wishing to be bound by any specific theory, it is believed that the absorbed light will induce alternating electric currents on the metal surface, and that this currents immediately re-emit light out of the metal. Upon this pigment light absorbing pigment microparticles are immobilized. Such pigment microparticles can be platelets, e.g., having a thickness that is substantially smaller than the planar dimension. For example five, ten or even 20 times smaller in thickness than in the planer. Such platelets can have a planer dimension less than 15 microns, but with a thickness less than 1 microns, more preferably with a planer dimension less than 12 microns but with a thickness less than 750 nm, even more preferably with a plan dimension less than 10 microns and a thickness less than 0.5 micron. The light absorbing microparticles can have D50[vol] value between 0.001 micron and 0.15 micron, more preferably between 0.002 micron and 0.1 micron and even more preferable between 0.005 micron and 0.075 micron.

The pigment microparticles can be both light scattering and absorbing for wavelengths of visible light. While not wishing to bound by any specific theory, it is believed that such pigments can provide both some visual effect of lightening the hair, without the need for bleaching with ammonia or monoethanolamine and hydrogen peroxide and some color. Such pigment microparticles can have a D50 [num] value between about 50 nm and about 750 nm, between about 100 nm and about 500 nm or between about 150 nm and about 400 nm. Such materials have a refractive index above about 1.5, above about 1.7 or above about 2.0.

According to an embodiment, a different pigment microparticles are combined to provide reflective, transmitting and refractive properties of the hair colored with the hair coloring composition described herein. A microparticle combination can be a material composite using at least two different pigment materials to form the pigment microparticles. In addition to, or alternating to, the microparticle combination, a mixture of separate pigment microparticles of different type can be used to bring about the desired reflective, transmitting and refractive properties.

The composite pigments, combination of pigments, and mixtures of pigment microparticles eliminate, or at least significantly reduce, hair penetration and scattering by light and thus eliminate pigment effect on perception of natural hair color change.

Pigment Concentration

The hair coloring composition for coloring hair fibers according to the present disclosure comprises microparticles comprising at least one pigment. The hair coloring composition comprises from about 0.01% to about 40%, about 0.05% to about 35%, about 0.1 to about 25%, or about 0.15% and about 20% pigment(s), by weight of the hair coloring composition.

Pigment Material

The material of the pigment microparticles can be inorganic or organic. Inorganic-organic mixed pigments are also possible.

According to an embodiment, inorganic pigment(s) are used. The advantage of inorganic pigment(s) is their excellent resistance to light, weather, and temperature. The inorganic pigment(s) can be of natural origin, and are, for example, derived from material selected from the group consisting of chalk, ochre, umber, green earth, burnt sienna, and graphite. The pigment(s) can preferably be white pigments, such as, for example, titanium dioxide or zinc oxide. The pigment(s) can also be colored pigments, such as, for example, ultra-marine or iron oxide red, luster pigments, metal effect pigments, pearlescent pigments, and fluorescent or phosphorescent pigments. The pigment(s) can be selected from the group consisting of metal oxides, hydroxides and oxide hydrates, mixed phase pigments, sulfur-containing silicates, metal sulfides, complex metal cyanides, metal sulfates, chromates and molybdates, and the metals themselves (bronze pigments). The pigment(s) can be selected from the group consisting of titanium dioxide (CI 77891), black iron oxide (CI 77499), yellow iron oxide (CI 77492), red and brown iron oxide (CI 77491), manganese violet (CI 77742), ultramarine (sodium aluminium sulfosilicates, CI 77007, Pigment Blue 29), chromium oxide hydrate (CI 77289), Prussian blue (ferric ferrocyanide, CI 77510), carmine (cochineal), zinc sulfide, barium sulfate, zinc oxide, siliconised titanium dioxide, siliconised zinc sulfide, siliconised zinc oxide, and mixtures thereof. The pigments) can be selected from the group consisting of iron oxide, titanium dioxide, mica, borosilicate, and combinations thereof. The pigment(s) can comprise an iron oxide (Fe2O3) pigment. The pigment(s) can comprise a combination of mica and titanium dioxide.

The pigment(s) can be pearlescent and colored pigment(s), and can preferably be based on mica which are coated with a metal oxide or a metal oxychloride, such as titanium dioxide or bismuth oxychloride, and optionally further color-imparting substances, such as iron oxides, Prussian blue, ultramarine, and carmine. The color exhibited by a pigment can be adjusted by varying the layer thickness. Such pigments are sold, for example, under the trade names Rona®, Colorona®, Dichrona®, RonaFlair®, Ronastar®, Xirona® and Timiron® all of which are available from Merck, Darmstadt, Germany. For example, Xirona® is a brand for color travel pigments that display color shifting effects depending on the viewing angle and are based on either natural mica, $SiO_2$ or calcium aluminium borosilicate flakes, coated with varying layers of $TiO_2$, Pigment(s) from the line KTZ® from Kobo Products, Inc., 3474 So. Clinton Ave., So. Plainfield, USA, are also useful herein, in particular the Surface Treated KTZ® Pearlescent Pigments from Kobo. Particularly useful are KTZ® FINE WHITE (mica and TiO2) having a D50 particle diameter of 5 to 25 micron and also KTZ® CELESTIAL LUSTER (mica and TiO2, 10 to 60 micron) as well as KTZ® CLASSIC WHITE (mica and TiO2, 10 to 60 micron). Also useful are SynCrystal Sapphire from Eckart Effect Pigments, which is a blue powder comprising platelets of synthetic fluorphlogopite coated with titanium dioxide, ferric ferrocyanide and small amounts of tin oxide. Also useful is SYNCRYSTAL Almond also from Eckart, which is a beige powder with a copper reflection color and is composed of platelets of synthetic fluorphlogopite and coated with titanium dioxide and iron oxides. Also useful is Duocrome® RV 524C from BASF, which provides a two color look via a lustrous red powder with a violet reflection powder due to its composition of mica, titanium dioxide and carmine. The colored pigment(s) can be lightly bright colored pigment(s), and can particularly be white color variations.

The pigment(s) can be organic pigments. The at least one pigment can be an organic pigment. As used herein, the term "organic pigment" means any pigment that satisfies the definition in Ullmann's encyclopedia in the chapter on organic pigments instance, the at least one organic pigment can be chosen from nitroso, nitro, azo, xanthene, quinoline, anthraquinone, phthalocyanin, copper phthalocyanin, copper hexadecachlorophthalocyanine, 2-[(2-Methoxy-4-nitrophenyl)azo]-N-(2-methoxyphenyl)-3-oxobutyramide, metal-complex, isoindolinone, isoirrdoline quinacridone, perinone, perylene, diketopyrrolopyrrole, thioindigo, dioxazine, triphenylmethane, dimethylquinacridone and quinophthalone compounds. Or the pigment can be at least one of uncolored and UV absorbing.

The organic pigment(s) can be selected from the group consisting of natural pigments sepia, gamboge, bone charcoal, Cassel brown, indigo, chlorophyll and other plant pigments. The synthetic organic pigments can be selected from the group consisting of azo pigments, anthraquinoids, indigoids, dioxazine, quinacridone, phthalocyanine, isoindolinone, perylene and perinone, metal complex, alkali blue, diketopyrrolopyrrole pigments, and combinations thereof. A particularly preferred pigment is 7-Bis(1,3-dichloropropan-2-yl)benzo[1 mn][3,8]phenanthrolin-1,3,6,8(2H, 7H)-tetraon.

According to an embodiment, the pigment(s) can be selected from the pigment group consisting of, including any combination thereof (with CI meaning color index and CAS meaning Chemical Abstract Number):
Pigment Yellow 1 (CI 11680), CAS #2512-29-0
Pigment Yellow 3 (CI 11710), CAS #6486-23-3
Pigment Yellow 104 (CI 15985), CAS #2783-94-0
Pigment Yellow 100 (CI 19140), CAS #1934-21-0
Pigment Yellow 16 (CI 20040), CAS #5979-28-2
Pigment Yellow 13 (CI 21100), CAS #5102-83-0
Pigment Yellow 83 (CI 21108), CAS #5567-15-7
Pigment Yellow 115 (CI 47005), CAS #8004-92-0/94891-32-4/95193-83-2/68814-04-0
Pigment Orange 1 (CI 11725), CAS #6371-96-6
Pigment Orange 39 (CI 45370), CAS #4372-02-5/596-03-2
Pigment Orange 43 (CI 71105), CAS #4424-06-0
Pigment Red 4 (CI 12085), CAS #2814-77-9
Pigment Red 3 (CI 12120), CAS #2425-85-6
Pigment Red 112 (CI 12370), CAS #6535-46-2
Pigment Red 7 (CI 12420), CAS #6471-51-8
Pigment Red 5 (CI 12490), CAS #6410-41-9
Pigment Red 68 (CI 15525), CAS #5850-80-6
Pigment Red 51 (CI 15580), CAS #5850-87-3
Pigment Red 49 (CI 15630), CAS #1248-18-6
Pigment Red 63 (CI 15800), CAS #6371-76-2
Pigment Red 57 (CI 15850), CAS #5858-81-1
Pigment Red 48 (CI 15865), CAS #3564-21-4/5280-66-0
Pigment Red 63 (CI 15880), CAS #6417-83-0
Pigment Red 83 (CI 58000), CAS #72-48-0
Pigment Red 181 (CI 73360), CAS #2379-74-0
Pigment Red 122 (CI 73915), CAS #980-26-7
Pigment Green 7 (CI 74260), CAS #1328-53-6
Food Blue 05:01 (CI 42051), CAS #3536-49-0
Pigment Blue 66 (CI 73000), CAS #482-89-3
Pigment Blue 16 (CI 74100), CAS #574-93-6
Pigment Blue 15 (CI 74160), CAS #147-14-8
Pigment Violet 23 (CI 51319), CAS #6358-30-1
Pigment Violet 36 (CI 73385), CAS #5462-29-3
Pigment Violet 19 (CI 73900), CAS #1047-16-1
Pigment Brown 1 (CI 12480), CAS #6410-40-8
Pigment Black 7 (CI 77266), CAS #1333-86-4

The pigment(s) used in the hair coloring composition can include at least two different pigments selected from the above pigment group, or can include at least three different pigments selected from the above pigment group.

According to an embodiment, the pigment(s) used in the hair coloring composition can include at least one yellow pigment selected from the yellow pigment group consisting of:
Pigment Yellow 1 (CI 11680), CAS #2512-29-0
Pigment Yellow 3 (CI 11710), CAS #6486-23-3
Pigment Yellow 104 (CI 15985), CAS #2783-94-0
Pigment Yellow 100 (CI 19140), CAS #1934-21-0
Pigment Yellow 16 (CI 20040), CAS #5979-28-2.
Pigment Yellow 13 (CI 21100), CAS #5102-83-0
Pigment Yellow 83 (CI 21108), CAS #5567-15-7
Pigment Yellow 115 (CI 47005), CAS #8004-92-0/94891-32-4/95193-83-2/68814-04-0

In addition to the at least one yellow pigment, or alternatively, the pigments(s) used in the hair coloring composition can include at least one red pigment selected from the yellow pigment group consisting of:
Pigment Red 4 (CI 12085), CAS #2814-77-9
Pigment Red 3 (CI 12120), CAS #2425-85-6

Pigment Red 112 (CI 12370), CAS #6535-46-2
Pigment Red 7 (CI 12420), CAS #6471-51-8
Pigment Red 5 (CI 12490), CAS #6410-41-9
Pigment Red 68 (CI 15525), CAS #5850-80-6
Pigment Red 51 (CI 15580), CAS #5850-87-3
Pigment Red 49 (CI 15630), CAS #1248-18-6
Pigment Red 63 (CI 15800), CAS #6371-76-2
Pigment Red 57 (CI 15850), CAS #5858-81-1
Pigment Red 48 (CI 15865), CAS #3564-21-4/5280-66-0
Pigment Red 63 (CI 15880), CAS #6417-83-0
Pigment Red 83 (CI 58000), CAS #72-48-0
Pigment Red 181 (CI 73360), CAS #2379-74-0
Pigment Red 122 (CI 73915), CAS #980-26-7.

In addition to the at least one yellow pigment and/or the at least one red pigment, or alternatively, the pigments(s) used in the hair coloring composition can include at least one green pigment selected from the green pigment group consisting of:
Pigment Green 7 (CI 74260), CAS #1328-53-6.

The pigment(s) can have a surface zeta potential of ≥±15 mV, preferably ≥±20 mV, more preferably ≥±25 mV. The surface zeta potential can be measured with a zetasizer, for example, a Zetasizer 3000 HS. Surface zeta potential measurements are conducted, for example, according to ISO 13099.

For example, the white or colored organic pigments can be chosen from carmine, carbon black, aniline black, melanin, azo yellow, quinacridone, phthalocyanin blue, sorghum red, the blue pigments codified in the Color Index under the references CI 42090, 69800, 69825, 73000, 74100, and 74160, the yellow pigments codified in the Color Index under the references CI 11680, 11710, 15985, 19140, 20040, 21100, 21108, 47000, and 47005, the green pigments codified in the Color Index under the references CI 61565, 61570, and 74260, the orange pigments codified in the Color Index under the references CI 11725, 15510, 45370, and 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915, and 75470, and the pigments obtained by oxidative polymerization of indole or phenolic derivatives as described in French Patent Publication No. FR 2 679 771.

Non-limiting examples that can also be mentioned include pigmentary pastes of organic pigments, such as the products sold by the company Hoechst under the names: JAUNE COSMENYL IOG: Pigment Yellow 3 (CI 11710); JAUNE COSMENYL G: Pigment Yellow 1 (CI 11680); ORANGE COSMENYL GR: Pigment Orange 43 (CI 71105); ROUGE COSMENYL R: Pigment Red 4 (CI 12085); CARMINE COSMENYL FB: Pigment Red 5 (CI 12490); VIOLET COSMENYL RL: Pigment Violet 23 (CI 51319); BLEU COSMENYL A2R: Pigment Blue 15.1 (CI 74160); VERT COSMENYL GG: Pigment Green 7 (CI 74260); and NOIR COSMENYL R:
Pigment Black 7 (CI 77266), while known as an organic pigment, is also known as a darkening pigment.

The at least one pigment in accordance with the present disclosure can also be in the form of at least one composite pigment as described in European Patent Publication No. EP 1 184 426 A2. These composite pigments can be, for example, compounds of particles comprising a mineral core, at least one binder for ensuring the binding of the organic pigments to the core, and at least one organic pigment at least partially covering the core.

The at least one pigment in accordance with the present disclosure can be in the form of small undissolved microparticles, which do not diffuse into the hair color, but deposit on the outer wall of the keratin fiber. Suitable color pigments can be of organic and/or inorganic origin. But the pigments can also be inorganic color pigments, given the excellent light, weather and/or temperature resistance thereof.

Inorganic Pigment Materials

According to an embodiment, at least one inorganic pigment(s) are used. The advantage of inorganic pigment(s) is their excellent resistance to light, weather, and temperature. Inorganic pigments, whether natural or synthetic in origin, include those produced from chalk, red ocher, umbra, green earth, burnt sienna or graphite, for example. Furthermore, it is possible to use black pigments, such as iron oxide black, color pigments such as ultramarine or iron oxide red, and fluorescent or phosphorescent pigments as inorganic color pigments.

Colored metal oxides, metal hydroxides and metal oxide hydrates, mixed phase pigments, sulfurous silicates, silicates, metal sulfides, complex metal cyanides, metal sulfates, metal chromates and/or metal molybdates are particularly suitable. In particular, preferred color pigments are black iron oxide (CI 77499), yellow iron oxide (CI 77492), red and brown iron oxide (CI 77491), manganese violet (CI 77742), ultramarine (sodium aluminum sulfosilicates, CI 77007, Pigment Blue 29), chromium oxide hydrate (CI 77289), iron blue (ferric ferrocyanide, CI 77510) and/or carmine (cochineal).

The pigment(s) can be pearlescent and colored pigment(s), and can preferably be based on mica which are coated with a metal oxide or a metal oxychloride, such as titanium dioxide or bismuth oxychloride, and optionally further color-imparting substances, such as iron oxides, Prussian blue, ultramarine, and carmine. The color exhibited by a pigment can be adjusted by varying the layer thickness. Such pigments are sold, for example, under the trade names Rona®, Colorona®, Dichrona®, RonaFlair® and Timiron® all of which are available from Merck, Darmstadt, Germany. Pigment(s) from the line KTZ® from Kobo Products, Inc., 3474 So. Clinton Ave., So. Plainfield, USA, are also useful herein, in particular the Surface Treated KTZ® Pearlescent Pigments from Kobo. Particularly useful are KTZ® FINE WHITE (mica and TiO2) having a D50 particle diameter of 5 to 25 micron. Also useful is Duocrome® RV 524C from BASF, which provides a two color look via a lustrous red powder with a violet reflection powder due to its composition of mica, titanium dioxide and carmine. The colored pigment(s) can be lightly bright colored pigment(s), and can particularly be white color variations.

These are usually mica-based and can be coated with one or more metal oxides from the group consisting of titanium dioxide (CI 77891), black iron oxide (CI 77499), yellow iron oxide (CI 77492), red and brown iron oxide (CI 77491, CI 77499), manganese violet (CI 77742), ultramarine (sodium aluminum sulfosilicates, CI 77007, Pigment Blue 29), chromium oxide hydrate (CI 77289), chromium oxide (CI 77288) and/or iron blue (ferric ferrocyanide, CI 77510).

Mica forms part of the phyllosilicates, including muscovite, phlogopite, paragonite, biotite, lepidolite, and margarite. To produce the pearlescing pigments in combination with metal oxides, the mica, primarily muscovite or phlogopite, is coated with a metal oxide.

As an alternative to natural mica, it is also optionally possible to use synthetic mica coated with one or more metal oxides as the pearlescing pigment. Such suitable pearlescing pigments based on natural micas are described in, e.g., WO 2005/065632. The at least one pigment can also be pearlescing pigments based on natural or synthetic mica and are coated with one or more of the aforementioned metal oxides. The color of the respective pigments can be varied by varying the layer thickness of the metal oxide or metal oxides.

The at least one pigment can also be at least one inorganic color pigment selected from the group consisting of colored metal oxides, metal hydroxides, metal oxide hydrates, silicates, metal sulfides, complex metal cyanides, metal sulfates, bronze pigments and/or colored pigments based on mica, which are coated with at least one metal oxide and/or a metal oxychloride.

The at least one pigment can also be at least one mica-based colored pigment, which is coated with one or more metal oxides from the group consisting of titanium dioxide (CI 77891), black iron oxide (CI 77499), yellow iron oxide (CI 77492), red and/or brown iron oxide (CI 77491, CI 77499), manganese violet (CI 77742), ultramarine (sodium aluminum sulfosilicates, CI 77007, Pigment Blue 29), chromium oxide hydrate (CI 77289), chromium oxide (CI 77288) and/or iron blue (ferric ferrocyanide, CI 77510).

The at least one pigment can also be color pigments commercially available, for example, under the trade names Rona®, Colorona®, Dichrona® and Timiron® from Merck, Ariabel® and Unipure® from Sensient, Prestige® from Eckart Cosmetic Colors, and Sunshine® from Sunstar.

The at least one pigment can also be color pigments bearing the trade name Colorona® are, for example: Colorona Copper, Merck, MICA, CI 77491 (IRON OXIDES); Colorona Passion Orange, Merck, Mica, CI 77491 (Iron Oxides), Alumina; Colorona Patina Silver, Merck, MICA, CI 77499 (IRON OXIDES), CI 77891 (TITANIUM DIOXIDE); Colorona RY, Merck, CI 77891 (TITANIUM DIOXIDE), MICA, CI 75470 (CARMINE); Colorona Oriental Beige, Merck, MICA, CI 77891 (TITANIUM DIOXIDE), CI 77491 (IRON OXIDES); Colorona Dark Blue, Merck, MICA, TITANIUM DIOXIDE, FERRIC FERROCYANIDE; Colorona Chameleon, Merck, CI 77491 (IRON OXIDES), MICA; Colorona Aborigine Amber, Merck, MICA, CI 77499 (IRON OXIDES), CI 77891 (TITANIUM DIOXIDE); Colorona Blackstar Blue, Merck, CI 77499 (IRON OXIDES), MICA; Colorona Patagonian Purple, Merck, MICA, CI 77491 (IRON OXIDES), CI 77891 (TITANIUM DIOXIDE), CI 77510 (FERRIC FERROCYANIDE); Colorona Red Brown, Merck, MICA, CI 77491 (IRON OXIDES), CI 77891 (TITANIUM DIOXIDE); Colorona Russet, Merck, CI 77491 (TITANIUM DIOXIDE), MICA, CI 77891 (IRON OXIDES); Colorona Imperial Red, Merck, MICA, TITANIUM DIOXIDE (CI 77891), D&C RED NO. 30 (CI 73360); Colorona Majestic Green, Merck, CI 77891 (TITANIUM DIOXIDE), MICA, CI 77288 (CHROMIUM OXIDE GREENS); Colorona Light Blue, Merck, MICA, TITANIUM DIOXIDE: (CI 77891), FERRIC FERROCYANIDE (CI 77510); Colorona Red Gold, Merck, MICA, CI 77891 (TITANIUM DIOXIDE), CI 77491 (IRON); Colorona Gold Plus MP 25, Merck, MICA, TITANIUM DIOXIDE (CI 77891), IRON OXIDES (CI 77491); Colorona Carmine Red, Merck, MICA, TITANIUM DIOXIDE, CARMINE Colorona Blackstar Green, Merck, MICA, CI 77499 (IRON OXIDES); Colorona Bordeaux, Merck, MICA, CI 77491 (IRON OXIDES); Colorona Bronze, Merck, MICA, CI 77491 (IRON OXIDES); Colorona Bronze Fine, Merck, MICA, CI 77491 (IRON OXIDES); Colorona Fine Gold MP 20, Merck, MICA, CI 77891 (fTITANIUM DIOXIDE), CI 77491 (IRON OXIDES); Colorona Sienna Fine, Merck, CI 77491 (IRON OXIDES), MICA Colorona Sienna, Merck, MICA, CI 77491 (IRON OXIDES); Colorona Precious Gold, Merck, Mica, CI 77891 (Titanium dioxide), Silica, CI 77491 (Iron oxides), Tin oxide; Colorona Sun Gold Sparkle MP 29, Merck, MICA, TITANIUM DIOXIDE, IRON OXIDES, MICA, CI 77891, CI 77491 (EU); Colorona Mica Black, Merck, CI 77499 (Iron oxides), Mica, CI 77891 (Titanium dioxide) Colorona Bright Gold, Merck, Mica, CI 77891 (Titanium dioxide), CI 77491 (Iron oxides); Colorona Blackstar Gold, Merck, MICA, CI 77499 (IRON OXIDES); color pigments bearing the trade name Unipure® are, for example: Unipure Red LC 381 EM, Sensient CI 77491 (Iron Oxides), Silica; Unipure Black LC 989 EM, Sensient, CI 77499 (Iron Oxides), Silica; Unipure Yellow LC 182 EM, Sensient, CI 77492 (Iron Oxides), Silica.

Metal based pigments are also available, for example those sold by Toyal Europe within the Cosmicolor® Celeste range; Rose Pink, Iris Blue, Morpho Blue, Tecla Green, Aqua Green, Lunar Gold, Meadow Gold, Ivy Orange, Cherry Pink, Maple Red and Papilio Black, Crystal Silver, Frost Silver and Velvet Silver and within their Cosmicolor® Metallics range; Mirror Silver, Fine Silver, Bright Silver, Classic Silver and Sparkle Silver and within their Cosmicolor® Stratone range Honey Pink. Also useful are flakes sold by Eckart, for example Silverdream® range L-55350, Prismatic H-50550, Prismatic H-115002, Prismatic H-50720 and within their Visonaire® range; Splendid Silver Sea, Bright Silver Sea, Sparkling Silver Sea. Examples from Silberline within their EternaBrite® range include; 651-PA, Premier 251-PA, Premier 255-PA, Premier 351-PA and within their SparkleBrite® range 270NL-PA, 320NL-PA, Premier 2052NL-PA, Premier 2200NL-PA, Ultra 012NL-Pac, Ultra 011, Ultra 014, Ultra 015 and within their Sil-O-Wet® range 651-PA, 2052NL-PA and within their StarBrite® VMP range 2100, 3102, 4102, 5102, 6108 and from their Silvet® range; AD 007, AD 010, AD 013, AD 015, AD Premier 011, AD Premier 016. AD Ultra 011, AD Ultra 014, AD Ultra 015. Some pigments may be coated with surface treatment for example, but not limited to, silica to improve the stability within water based products. Some of the pigments may also have organic pigments adhered on their surface by a polymer binder to provide color as well as light reflections. For examples from Toyal Europe sold under the brand of Friend Color™ such as their Red Pigments, D 111 RE, D 462 RE and D 451 RE, their Blue Pigments, D 851 BL, D 462 BL and D 452 BL, their Yellow Pigments D 851 YE, D 462 YE and 452 YE and their Green Pigment D 462 GR.

Depending on the degree of the change in color that is desired on the keratin fiber, the at least one pigment can also be can be used in varying amounts. The more color pigment that is used, the higher is the extent of the change in color in general. Starting at a certain usage amount, however, the adherence of the pigments to the keratin fiber approaches a limiting value, beyond which it is no longer possible to increase the extent of the change in color by further increasing the pigment amount used. While not wishing to be bound by any specific theory, it is believed that when a certain thickness is achieved, an insignificant amount of the incident lights passes through the pigment layer to make a difference to the observed color due to the hair itself. The rest of the light is either scattered back towards the surface, or absorbed.

The at least one pigment can be partially (Scheme 1, (b), where the dark oval represents a pigment, even though the pigment can be white or colorless) or completely enveloped in a matrix (e.g., a polymer matrix or an inorganic matrix;

(Scheme 1, (a)). Or the pigment can be adhered to the surface of a matrix that can be colored or colorless (Scheme 1 (c)).

Scheme 1

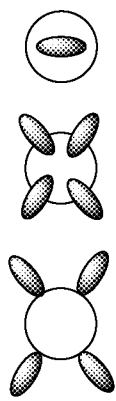

(a)

(b)

(c)

The matrix can be, e.g., $CaCO_3$, $MnCO_3$. Or the matrix can be a melamine formaldehyde matrix.

In another example, the at least one pigment can be encapsulated in silica, as described in Published U.S. Appl. No. 2007/0134180. Other examples of encapsulated pigments include encapsulated Carmine, Iron Oxides, Titanium dioxide, and Chrome Oxide/Hydroxide, the colorants D&C Red 21 Aluminum Lake, D&C Red 7 Calcium Lake, D&C Green 6 Liposoluble, and Aluminium Blue #1 (Indigo Carmine Lake). The encapsulated pigment can be titanium dioxide (used to lighten other pigments and to lend opacity to formulations) in any one of its mineral forms anatase, brookite or rutile, or mixtures thereof. Or the pigment can be at least one iron oxide in any of the 3 basic colors—red, black and yellow iron oxides, or mixtures thereof. From these 3 oxides and the addition of titanium dioxide, any shade of brown (skin tones) can be achieved.

The organic pigment(s) can have any suitable shape, including substantially spherical as defined herein before under the name of microspheres. But the organic pigment(s) can also be oval, elliptical, tubular, irregular, etc., or even combinations of various shapes.

According to an embodiment, the organic pigment(s) can include organic pigment(s) of different shape. Organic pigments having different shape can also be formed of different pigment materials. Furthermore, organic pigments having different shape can also formed of different pigment material to provide different color.

Depending on the shape, the organic pigment(s) can have a D50[vol] particle diameter of from 0.001 micron to 1 micron. For example, organic pigment(s) can have a D50 [vol] particle diameter of from 0.01 micron to 1 micron, preferably of from 0.015 micron to 0.75 micron, more preferably of from 0.02 micron to 0.50 micron. The terms "micron" and "microns" describe the size in micrometers [μm].

The organic pigment(s) can be light absorbing, but which for wavelengths of visible light provide negligible to low or no scattering. While not wishing to bound by any specific theory, it is believed that such pigments can provide more chromatic colors. Such organic pigment(s) can have a D50 [vol] value between about 0.001 micron and about 0.15 micron, between about 0.005 micron and about 0.10 micron or between about 0.010 micron and about 0.090 micron.

Inorganic-Organic Pigments

The organic pigment can also be a lake. As used herein, the term "lake" means at least one dye adsorbed onto insoluble particles, the assembly thus obtained remaining insoluble during use. The inorganic substrates onto which the dyes are adsorbed can be, for example, alumina, silica, calcium sodium borosilicate, calcium aluminum borosilicate, calcium carbonate, manganese carbonate, and aluminum. Among the dyes, non-limiting mention can be made of cochineal carmine. Non-limiting mention can also be made of the dyes known under the following names: D&C Red 21 (CI 45 380), D&C Orange 5 (CI 45 370), D&C Red 27 (CI 45 410), D&C Orange 10 (CI 45 425), D&C Red 3 (CI 45 430), D&C Red 4 (CI 15 510), D&C Red 33 (CI 17 200), D&C Yellow 5 (CI 19 140), D&C Yellow 6 (CI 15 985), D&C Green (CI 61 570), D&C Yellow 1 O (CI 77 002), D&C Green 3 (CI 42 053), and D&C Blue 1 (CI 42 090). A non-limiting example of a lake that can be mentioned is the product known under the following name: D&C Red 7 (CI 15 850:1).

The lake microparticles can have any suitable shape, including substantially spherical which can be described as microspheres as defined herein above. But the lake microparticles can also be oval, elliptical, tubular, irregular, etc., or even combinations of various shapes. According to an embodiment, the pigments can include lake microparticles of different shapes. For example, microparticles of different size can be used to provide different reflecting and absorbing properties. Microparticles having different shapes can also be formed of different pigment materials. Furthermore, microparticles having different shape can also formed of different pigment material to provide different color.

Depending on the shape, the lake pigments can have a D50[vol] particle diameter of from 0.001 micron to 1 micron. The microspheres can also have a D50[vol] particle diameter of from 0.05 micron to 0.70 micron, preferably of from 0.08 micron to 0.60 micron, and more preferably between of from 0.10 micron to 0.50 micron, such as from 0.15 micron to 0.40 micron, or such as of from 0.17 micron to 0.32 micron. The terms "micron" and "microns" describe the size in micrometers [μm].

According to an embodiment, pigment particles are referred to as being microspheres can be used for light-scattering and/or light absorbing purposes. Those particles, due to their pigment material, impart the hair with a specific color.

The at least one pigment in accordance with the present disclosure can also be in the form of at least one composite pigment as described in European Patent Publication No. EP 1 184 426 A2. These composite pigments can be, for example, compounds of particles comprising a mineral core, at least one binder for ensuring the binding of the organic pigments to the core, and at least one organic pigment at least partially covering the core.

Composite Microparticles, Combination of Microparticles, Mixtures of Microparticles The pigment microparticles can be a composite formed by two different types of pigment microparticles. Examples include a composite of a 2-dimensional microparticle and at least one microspherical particle (microsphere), a composite of different microspherical particles, and a composite of different 2-dimensional particles. Composite particles formed by 2-dimensional microparticles to which microspherical particles adhere provide an attractive alternative to a pure mixture of 2-dimensional microparticles and microspherical particles. For example, a metallic 2-dimensional microparticle can carry one or more microspherical particle such as one or more organic microspherical particle. The microspherical particles attached or bonded to the 2-dimensional microparticle can be formed of the same pigment material or can be formed of different pigment material. Composite microparticles formed of 2-dimensional microparticles and microspherical particles can provide multiple functionality in one particle such as (metallic) reflectance and dielectric scattering, reflectance and absorption.

Pigment microparticles can be composite material comprising a core of pigments made from metal like materials which can conduct electricity, and which can absorb light and re-emit the light out of the metal to give the appearance of strong reflectance. While not wishing to be bound by any specific theory, it is believed that the absorbed light will induce alternating electric currents on the metal surface, and that this currents immediately re-emit light out of the metal. Upon this pigment light absorbing pigment microparticles are immobilized. Such pigment microparticles can be platelets, e.g., having a thickness that is substantially smaller than the planar dimension. For example, five, ten or even 20 times smaller in thickness than in the planer. Such platelets can have a planer dimension less than 15 microns, but with a thickness less than 1 microns, more preferably with a planer dimension less than 12 microns but with a thickness less than 750 nm, even more preferably with a plan dimension less than 10 microns and a thickness less than 0.5 micron. The light absorbing microparticles can have D50 [vol] value between 0.001 micron and 0.15 micron, more preferably between 0.002 micron and 0.1 micron and even more preferable between 0.005 micron and 0.075 micron.

The pigment microparticles can be both light scattering and absorbing for wavelengths of visible light. While not wishing to bound by any specific theory, it is believed that such pigments can provide both some visual effect of lightening the hair, without the need for bleaching with ammonia or monoethanolamine and hydrogen peroxide and some color. Such pigment microparticles can have a D50 [num] value between about 0.050 micron and about 0.75 micron, between about 0.10 micron and about 0.5 micron or between about 0.15 micron and about 0.40 micron. Such materials have a refractive index above about 1.5, above about 1.7 or above about 2.0.

According to an embodiment, a different pigment microparticles are combined to provide reflective, transmitting and refractive properties of the hair colored with the hair coloring composition described herein. A microparticle combination can be a material composite using at least two different pigment materials to form the pigment microparticles. In addition to, or alternating to, the microparticle combination, a mixture of separate pigment microparticles of different type can be used to bring about the desired reflective, transmitting and refractive properties.

Additional Pigment Details

The hair coloring composition for coloring hair fibers according to the present disclosure comprises microparticles comprising at least one pigment. The hair coloring composition comprises from about 0.01% to about 40%, about 0.05% to about 35%, about 0.1 to about 25%, or about 0.15% and about 20% pigment(s) by weight of the hair coloring composition.

The pigment microparticles can be subjected to a surface treatment prior to suspending the particles in the carrier medium such as aqueous or solvent medium. The surface treatment aims for changing surface properties to improve wetting, dispersing, and stabilizing the microparticles in the carrier medium.

The pigment microparticles can have a "core-shell structure" (core-shell morphology) as described above for composition A. In the case that the pigment microparticles have a "core-shell structure", the "core" corresponds to the "naked" pigment or pigment material which provides the colorant properties as described herein. As such, embodiments also relate to a hair coloring composition including core-shell pigment microparticles, wherein the core of the pigment microparticles comprises an inorganic and/or organic pigment material, and wherein the shell of the pigment microparticles comprises at least one material for dispersing the pigment microparticles in the medium. The material for dispersing, also referred to as dispersant, can include, for example, a cationic polymer, a polymeric dispersant, and/or a surfactant. In another example, the at least one pigment can be encapsulated in silica, as described in Published U.S. Appl. No. 2007/0134180.

The pigment(s) can have a surface zeta potential of ≥±15 mV, preferably ≥±20 mV, more preferably ≥±25 mV. The surface zeta potential can be measured with a zetasizer, for example, a Zetasizer 3000 HS. Surface zeta potential measurements are conducted, for example, according to ISO 13099.

Depending on the degree of the change in color that is desired on the keratin fiber the at least one pigment can also be used in varying amounts. The more color pigment that is used, the higher is the extent of the change in color in general. Starting at a certain usage amount, however, the adherence of the pigments to the keratin fiber approaches a limiting value, beyond which it is no longer possible to increase the extent of the change in color by further increasing the pigment amount used. While not wishing to be bound by any specific theory, it is believed that when a certain thickness is achieved, an insignificant amount of the incident lights passes through the additional pigment layer added to make a difference to the observed color due to the hair itself. The rest of the light is either scattered back towards the surface, or absorbed.

Special Effect Pigments

The at least one pigment can also be a pigment with special effects. As used herein, the term "pigments with special effects" means pigments that generally create a non-uniform colored appearance (characterized by a certain shade, a certain vivacity, and a certain lightness) that changes as a function of the conditions of observation (light, temperature, observation angles, etc.). They thus contrast with white or colored pigments that afford a standard uniform opaque, semi-transparent, or transparent shade.

Several types of pigments with special effects exist, including those with a low refractive index, such as fluorescent, photochromic, or thermochromic pigments, and those with a high refractive index, such as nacres or glitter flakes. Examples of pigments with special effects of which non-limiting mention can be made include nacreous pigments such as mica coated with titanium or with bismuth oxychloride, colored nacreous pigments such as titanium mica with iron oxides, titanium mica for example with ferric blue or with chromium oxide, titanium mica with an organic pigment of the abovementioned type, and also nacreous pigments based on bismuth oxychloride. Nacreous pigments of which non-limiting mention can be made include the CELLINI nacres sold by Engelhard (mica-TiO$_2$-lake), PRESTIGE sold by Eckart (mica-TiO2), PRESTIGE BRONZE sold by Eckart (mica-Fe$_2$O$_3$), and COLORONA sold by Merck (mica-TiO$_2$—Fe$_2$O$_3$).

In addition to nacres on a mica support, multilayer pigments based on synthetic substrates such as alumina, silica, sodium calcium borosilicate, calcium aluminum borosilicate, and aluminum, can be envisaged.

Non-limiting mention can also be made of pigments with an interference effect that are not fixed onto a substrate, for instance liquid crystals (HELICONES HC from Wacker) and holographic interference flakes (GEOMETRIC PIGMENTS or SPECTRA F/X from Spectratek). Pigments with special effects also comprise fluorescent pigments, whether these are substances that are fluorescent in daylight or that produce an ultraviolet fluorescence, phosphorescent pigments, photochromic pigments, thermochromic pigments, and quantum dots, sold, for example, by the company Quantum Dots Corporation.

Quantum dots are luminescent semiconductive nanoparticles capable of emitting, under light excitation, irradiation with a wavelength ranging from 400 nm to 700 nm. These nanoparticles are known from the literature. They can be manufactured, for example, according to the processes described, for example, in U.S. Pat. No. 6,225,198 or 5,990,479, in the publications cited therein, and also in the following publications: Dabboussi B. O. et al. "(CdSe)ZnS core-shell quantum dots: synthesis and characterization of a size series of highly luminescent nanocrystallites" Journal of Physical Chemistry B, vol. 101, 1997 pp. 9463-9475 and Peng, Xiaogang et al "Epitaxial growth of highly luminescent CdSe/CdS core/shell nanocrystals with photostability and electronic accessibility", Journal of the American Chemical Society, vol. 119, No. 30, pp. 7019-7029.

The variety of pigments that can be used in the present disclosure makes it possible to obtain a wide range of colors, and also optical effects such as metallic effects or interference effects.

The pigments that can be used in the present disclosure can transmit light of various wavelengths, including visible light (e.g., light having a wavelength of above 350 nm). The pigment(s) can also transmit light of certain wavelengths, but also reflect light of certain wavelengths. And the pigment(s) can also be 100% reflective. For examples, reflective pigments provide a high specular reflection of visible light. Reflective pigments include those that are partially or completely coated with a non-matt and non-scattering surface layer of a metal or metal oxide. The substrate can be chosen from glasses, ceramics, graphite, metal oxides, aluminas, silicas, silicates, especially aluminosilicates and borosilicates and synthetic mica (e.g., fluorophlogopite), to name a few. The metal or metal oxide can be, without limitation, titanium oxides, iron oxides, tin oxide, chromium oxide, barium sulfate, MgF$_2$, CeF$_3$, ZnS, ZnSe, SiO$_2$, Al$_2$O$_3$, MgO, Y$_2$O$_3$, SeO$_3$, SiO, HfO$_2$, ZrO$_2$, CeO$_2$, Nb$_2$O$_5$, Ta$_2$O$_5$ and MoS$_2$, and mixtures thereof. Reflective pigments can have a spectral reflectance in the visible spectrum of at least 70%.

Other reflective pigments include those having non-goniochromatic layered structure of two or more polymeric and/or metallic layers of different refractive indices. For example, reflective particles comprising layers of 2,6-polyethylene naphthalate (PEN) and of polymethyl methacrylate are sold by 3M under the name Mirror Glitter™. Other effect pigments are available under the trade name Metasomes Standard/Glitter in various colors (yellow, red, green, blue) from Flora Tech.

Pigments can be chosen such that hair coloring composition embodiments of the present invention contain at least one pigment that can produce a darkening effect on hair (e.g., white hair) greater than 10 dL units, greater than 25 dL units, greater than 50 dL or greater than 75 dL, units with a level of 1% of that pigment. Such pigments can have a particle size of between 0.005 microns and 0.100 microns and/or a broad band absorbing profile. One example of such a pigment includes carbon black, including carbon black particles.

The darkening effect of the hair coloring composition embodiments of the present invention is determined by preparing a hair coloring composition comprising 1% total pigment (e.g., at least one organic pigment) by weight. A Minolta spectrophotometer CM-2600d is used to measure the color of the tresses before coloring occurs, on both the front and back sides, and the values are averaged. Two hair tresses (Kerling, Natural White special quality) have the hair coloring composition applied and brushed into the hair within a plastic weigh boat at level of 1 g per g of hair. The hair is then dried using a hairdrier while being combed to produce two tresses with individualised hair strands. A Minolta spectrophotometer CM-2600d is used to measure the color of the tresses, on both the front and back sides, and the values are averaged. dL value is calculated as:

$$dL = (L_{Initial} - L_{Colored})$$

wherein $L_{Initial}$ is the D65 L* value for the untreated hair tresses measured at the beginning of the experiment, and $L_{Colored}$ is the D65 L* values after coloring and drying of the same hair tresses.

Pigments can be chosen such that hair coloring composition embodiments of the present invention contain at least one pigment that can produce a lightening effect on dark hairof greater than 10 dL units, greater than 25 dL units, greater than 50 dL or greater than 75 dL units with a level of 10% of that pigment. Such pigments can have a particle size of 0.100 microns to 0.300 microns and/or a spherical morphology. Examples of such pigments include TiO$_2$, ZnO BN and combinations thereof.

The lightening effect of the hair coloring composition embodiments of the present invention is determined by preparing a hair coloring composition comprising 1% total pigment (e.g., at least one organic pigment) by weight. A Minolta spectrophotometer CM-2600d is used to measure the color of the tresses before coloring occurs, on both the front and back sides, and the values are averaged. Two hair tresses (Kerling, Level 3, special quality) have the hair coloring composition applied and brushed into the hair within a plastic weigh boat at level of 1 g per g of hair. The hair is then dried using a hairdrier while being combed to produce two tresses with individualised hair strands. A Minolta spectrophotometer CM-2600d is used to measure the color of the tresses, on both the front and back sides, and the values are averaged. dL value is calculated as:

$$dL = (L_{Colored} - L_{Initial})$$

wherein $L_{Initial}$ is the D65 L* value for the untreated hair tresses measured at the beginning of the experiment, and $L_{Colored}$ is the D65 L* values after coloring and drying of the same hair tresses.

Pigments can also be chosen such that hair coloring composition embodiments of the present invention contain at least one pigment that has a flake morphology, wherein a major axis is between 5 and 15 microns and a minor axis is between 0.05 and 0.5 microns. Such pigments can produce a lightening effect on hairgreater than 20 dL units with a level of 10% of the flake.

Combinations of pigments can also be used to effect, among other things, light-to-dark and dark-to-light transformations. For example, to effect a light-to-dark transformation, three chromatic organic pigments and carbon black can be combined to access a "brown" color space an a* value of 6 to 14 and a b* value of 5 to 30). Or to effect a dark-to-light transformation, three chromatic organic pigments and a white pigment can be combined to access a "brown" color space.

A "brown" color space can also be accessed by combining three chromatic organic pigments and a pigment having flake morphology; three pigments having flake morphology having organic pigments bound to the flake surface (e.g., a pigment having flake morphology having other pigments bound to their surface in a fashion similar to what is shown in Scheme 1(b) and (c), herein).

Pigments having flake morphology include pigments having a major axis between 5 and 15 microns and a minor axis between 0.01 and 0.5 microns, and where in the flake factor is greater than 10, more preferably more than 50, even more preferably more than 100, most preferably more than 200.

A "grey" color space can be accessed by combining three chromatic organic pigments (or flakes with pigments bound onto the surface), one white pigment (or flake), and one carbon black pigment.

E. The pH

The hair coloring composition component compositions A and B in accordance with the present disclosure can have a pH that enables the corresponding polymer to respectively be cationic and anionic. For composition A the pH will be acidic such as from about 3 to about 6.8 so as to protonate the amine groups. If the cationic polymer of composition A is a quaternary ammonium polymer, the pH may range from about 5 to about 7.5. For composition B, the pH will be basic so as to maintain the carboxyl or sulfonyl group as an anion. For composition B, for example, the pH can be 8 or higher, 9 or higher or at most 11. In some examples, the hair coloring composition B embodiments in accordance with the present invention can have a pH of from about 7.5 to about 11, about 8 to about 11 or about 7.5 to about 9. Accordingly, the pH may range from about 3 to about 8 for amine polymers that can form cationic groups, e.g., amines and the pH can range from about 6.8 to about 11 for anionic polymers that can form anionic groups, e.g., carboxylic and sulfonic acids. For amine polymers with cation forming groups (amines), preferably the pH is about 4 to about 7 and in many embodiments 6.8 or lower. For anionic polymers with anion forming groups (acids) the pH can be 8 or higher, 9 or higher or at most 11

The hair coloring composition component compositions A and Bin accordance with the present disclosure can comprise a pH modifier and/or buffering agent. The amount is sufficiently effective to adjust the pH of composition A or composition B to an appropriate range to maintain the cationic or anionic nature of the polymer respectively. Suitable pH modifiers and/or buffering agents for use herein include, but are not limited to: ammonia, alkanolamines such as monoethanolamine, di ethanolamine, triethanolamine, monopropanolamine, dipropanolamine, tripropanolamine, tripropanolamine, 2-amino-2-methyl-1-propanol, and 2-amino-2-hydroxymethyl-1,3,-propandiol and guanidium salts, alkali metal and ammonium hydroxides and carbonates, such as sodium hydroxide, sodium silicate, sodium meta silicate and ammonium carbonate, and acids such as inorganic and inorganic acids, e.g., phosphoric acid, acetic acid, ascorbic acid, citric acid or tartaric acid, hydrochloric acid, and mixtures thereof.

F. Dispersants

The pigment microparticles can be dispersed in composition A with the addition of at least one of a dispersant and a wetting agent. While not wishing to be bound by any specific theory, it is believed that only when the pigments are de-aggregated into their primary particles do they deliver the optimum optical performance. For examples, pigments with a primary particle size of 0.02 micron which provide brilliant bright colors, when present as aggregates of around 0.2 micron provide duller colors.

The pigment microparticles can also be dispersed through the use of high shear mixing; for example through use to the appropriate ball mill, ultra-high pressure homogenizer or other system known by those skilled in the art of pigment dispersion.

The dispersant serves to protect the pigment microparticles against agglomeration or flocculation either in the dry state or in the solvent. Wetting agents can be low molecular weight monomeric surfactants (for example, anionic, cationic or amphoteric surfactants). Dispersants can be higher molecular weight surface-active or pigment particle affinic polymers (for example, polyelectrolyte dispersants such as maleic acid copolymers, and polyurethanes or polyacrylates containing carboxylic acid, amine or isocyanate pigment affinic anchor groups or polyethylene imines) or other type of polyelectrolytes.

The dispersant can be a surfactant, an oligomer (e.g., example, oligomers have up to 20 monomeric units, polymers have at least 20 monomeric units), a polymer, or a mixture of several thereof, bearing at least one functional group with strong affinity for the surface of the pigment microparticles. For example, they can physically or chemically attach to the surface of the pigment microparticles. These dispersants also contain at least one functional group that is compatible with or soluble in the continuous medium. For example, 12-hydroxystearic acid esters and $C_8$ to $C_{20}$ fatty acid esters of polyols such as glycerol or diglycerol are used, such as poly(12-hydroxystearic acid) stearate with a molecular weight of about 750 g/mol, such as the product sold under the name SOLSPERSE 21,000 by the company Avecia, polyglyceryl-2 dipolyhydroxystearate (CTFA name) sold under the reference DEHYMYLS PGPH by the company Henkel, or polyhydroxystearic acid such as the product sold under the reference ARLACEL P100 by the company Uniqema, and mixtures thereof. Similar dispersants will function to disperse the polar functional silicone polymers that are not readily dispersible and/or are not at least partially soluble in aqueous media.

As other dispersants that can be used in the hair coloring composition of the present disclosure, non-limiting mention can be made of quaternary ammonium derivatives of polycondensed fatty acids, for instance SOLSPERSE 17,000 sold by the company Avecia, and polydimethylsiloxane/ oxypropylene mixtures such as those sold by the company Dow Corning under the references DC2-5185 and DC2-5225 C.

Representative wetting agents include those available from a variety of suppliers including Air Products and Chemicals (e.g., CARBOWET™ GA-210 surfactant which has a viscosity of 80 cps, CARBOWET GA-221 surfactant which has a viscosity of 100 cps, DYNOL™ 607 superwetter which has a viscosity of 205 cps and DYNOL 800 superwetter which has a viscosity of 230 cps); Dow Chemical Co. (e.g., CAPSTONE™ fluorosurfactants FS 31, FS 34, FS 35, FS 61 and FS 64); and Stepan Company (e.g., STEPWET™ DOS-70 surfactant which contains 70% active ingredients and has a viscosity of 200 cps, and STEPWET DOS-70EA surfactant which contains 70% active ingredients and has a viscosity of 220 cps).

Representative dispersants are also available from a variety of suppliers, and include various nonionic (e.g., ethoxylated) and anionic (e.g., non-ethoxylated salt) forms including agents from Air Products and Chemicals, Inc. (e.g., SURFYNOL™ PSA336); Archer Daniels Midland Co. (e.g., ULTRALEC™ F deoiled lecithin); Ashland Inc. (e.g., NEKAL™ WS-25-I, which is a sodium bis(2,6-dimethyl 4heptyl)sulfosuccinate); BASF (e.g., DISPEX™ AA 4144, DISPEX ULTRA FA 4425 which is a fatty acid-modified emulsifier having a viscosity of 40,000 cps, DISPEX ULTRA FA 4420 which is a fatty acid-modified emulsifier and a dark brown liquid of unspecified viscosity, DISPEX ULTRA FA 4431 which is an aliphatic polyether with acidic groups having a viscosity of 350 cps, DISPEX ULTRA PA 4501 which is a fatty acid modified polymer having a viscosity of 10,000 cps, DISPEX ULTRA PA 4510, EFKA™ PU 4010, EFKA PU 4047 which is a modified polyurethane, EFKA PX 4300, EFKA ULTRA PA 4510 and EFKA ULTRA PA 4530 which are modified polyacrylates, EFKA FA 4620 which is an acidic polyether having a viscosity of 1,400 cps, EFKA FA 4642 which is an unsaturated polyamide and acid ester salt having a viscosity of 2,000 cps, HYDROPALAT™ WE 3135, HYDROPALAT WE 3136 and HYDROPALAT WE 3317 which are difunctional block copolymer surfactants terminating in primary hydroxyl groups and having respective viscosities of 375, 450 and 600 cps, and TETRONIC™ 901 and TERTRONIC 904 which are tetrafunctional block copolymers terminating in primary hydroxyl groups and having respective viscosities of 700 and 320 cps); Borchers BORCHI™ Gen 0151 which is a polyurethane oligomer having a viscosity of about 30,000 cps, BORCHI Gen 0652 which is an amine neutralized acrylic acid copolymer having a viscosity of about 75-300 cps, and BORCHI Gen 1252 and BORCHI Gen 1253 which are acrylic ester copolymers having respective viscosities of about 1,500-3,500 and 50-300 cps); Byk-Chemie (e.g., BYK™ 156 which is a solution of an ammonium salt of an acrylate copolymer, DISPERBYK™ which is a solution of an alkyl ammonium salt of a low-molecular-weight polycarboxylic acid polymer, DISPERBYK-102 which is an acidic copolymer, DISPERBYKT™-145 which is a phosphoric ester salt of a high molecular copolymer with pigment affinic groups and a liquid of unspecified viscosity, DISPERBYK-190 which is a solution of a high molecular weight block copolymer with pigment affinic groups, DISPERBYK-2013 which is a structured copolymer with pigment affinic groups having a viscosity of 8,600 cps, DISPERBYK-2055 which is a copolymer with pigment affinic groups and a liquid of unspecified viscosity, DISPERBYK-2060 which is a solution of a copolymer with pigment affinic groups having a viscosity of 3,600 cps, DISPERBYK-2061 which is a solution of a copolymer with pigment affinic groups having a viscosity of 491 cps, DISPERBYK-2091, DISPERBYK-2200 which is a high molecular weight copolymer with pigment affinic groups sold in solid form as pastilles and BYKJET™-9152 which is a copolymer with pigment affinic groups having a viscosity of 21,600 cps); Clariant (e.g., DISPERSOGEN™ 1728 which is an aqueous solution of a novolac derivative having a viscosity of 4,000 cps, DISPEROGEN 2774 which is a novolac alkoxylate having a viscosity of 4,000 cps, GENAPOL™ X 1003 and GENAPOL X 1005 which are fatty alcohol ethoxylates having respective viscosities of about 400 cps and 1,300 cps, HOSTAPAL BV concentrate which is a sulfate ester having a viscosity of about 2,700 cps); Cray Valley (e.g., SMA1440H which is an ammonia salt of a styrene maleic anhydride copolymer solution); Dow Chemical Co. (e.g., the TAMOL™ family of dispersants including TAMOL 165A and TAMOL 731A); Elementis (e.g., NUOSPERSE™ FA196 which has a viscosity of 1,200 cps); Lubrizol (e.g., SOLSPERSE™ 27000, SOLSPERSE 28000, SOLSPERSE 32000, SOLSPERSE 39000, SOLSPERSE 64000, SOLSPERSE 65000, SOLSPERSE 66000, SOLSPERSE 71000, SOLSPERSE M387, SOLPLUS™ R700 and SOLPLUS K500); Ethox Chemicals, LLC (e.g., the E-SPERSE™ family of dispersants and ETHOX™ 4658); Evonik (e.g., TEGO™ DISPERS 656, TEGO DISPERS 685, TEGO DISPERS 750W and TEGO DISPERS 757W); Rhodia Solvay Group (e.g., ABEX 2514 and ABEX 2525 which are nonionic surfactants, RHODACAL™ IPAM which is isopropyl amine dodecylbenzene sulfonate having a viscosity of 10,000 cps, RHODAFAC™ RS-710 which is a polyoxyethylene tridecyl phosphate ester, and the RHODOLINE™ family of dispersants including RHODOLINE 4170 and RHODOLINE 4188); Sasol Wax GmbH (e.g., ADSPERSE™ 100, ADSPERSE 500 and ADSPERSE 868) and Stepan Company (e.g., G-3300 which is an isopropyl amine salt of an alkyl aryl sulfonate having a viscosity of about 6000 cps, POLYSTEP™ A-15 which is a sodium dodecylbenzene sulfonate having a viscosity of about 85 cps, POLYSTEP B-11 and POLYSTEP B-23 which are ethoxylated ammonium lauryl ether sulfates respectively containing 4 or 12 moles of ethylene oxide and having respective viscosities of 66 and 42 cps, and POLYSTEP B-24 which is sodium lauryl sulfate having a viscosity of 100 cps).

Other examples of dispersants include dispersants from the product lines of DisperByk (BYK), Solsperse (Lubrizol), Solplus (Lubrizol), Tego Dispers (Evonik), Tego Wet (Evonik), and EFKA (BASF). Examples of the dispersive additive include, but not limited to, Disperbyk 102, Disperbyk 103, Disperbyk 106, Disperbyk 107, Disperbyk 108, Disperbyk 109, Disperbyk 110, Disperbyk 111, Disperbyk 115, Disperbyk 118, Disperbyk 140, Disperbyk 142, Disperbyk 145, Disperbyk 161, Disperbyk 162, Disperbyk 163, Disperbyk 164, Disperbyk 167, Disperbyk_168, Disperbyk 170, Disperbyk 171, Disperbyk 174, Disperbyk 180, Disperbyk 181, Disperbyk 182, Disperbyk 184, Disperbyk 185, Disperbyk 187, Disperbyk 190, Disperbyk 191, Disperbyk 192, Disperbyk 193, Disperbyk 194N, Disperbyk 199, Disperbyk 2000, Disperbyk 2001, Disperbyk 2008, Disperbyk 2009, Disperbyk 2010, Disperbyk 2012, Disperbyk 2013, Disperbyk 2015, Disperbyk 2022, Disperbyk 2025, Disperbyk 2050, Disperbyk 2055, Disperbyk 2060, Disperbyk 2061, Disperbyk 2096, Disperbyk 2117, Disperbyk 2118, Disperbyk 2150, Disperbyk 2151, Disperbyk 2152, Disperbyk 2155, Disperbyk 2163, Disperbyk 2164, Disperbyk 2200, Tego Dispers 630, Tego Dispers 650, Tego Dispers 652, Tego Dispers 653, Tego Dispers 656, Tego Dispers 660 C, Tego Dispers 670, Tego Dispers 671, Tego Dispers 672, Tego Dispers 685, Tego Dispers 688, Tego Dispers 700, Tego Dispers 710, Tego Dispers 735 W, Tego Dispers 740 W, Tego Dispers 745 W, Tego Dispers 750 W, Tego Dispers 752 W, Tego Dispers 755 W, Tego Dispers 757 W, ego Dispers 760 W, Tego Dispers 761 W, Tego Wet 240, Tego Wet 250, Tego Wet 251, Tego Wet 260, Tego Wet 265, Tego Wet 270, Tego Wet 280, Tego Wet 500, Tego Wet 505, Tego Wet 510, Tego Wet KL245, EFKA 6220, EFKA 6225, and combinations thereof.

The dispersant can be a polyolefin polymer. These dispersants include but are not limited to an olefinic polymer having a molecular weight of about 100 g/mol to about 5,000,000 g/mol, such as about 1,000 g/mol to about 1,000,000 g/mol. Examples of polymers, include, but are not limited to poly(ethylene), poly(propylene), poly(hutylene), poly(isobutylene), poly(isoprene), poly(acetal), poly(ethylene glycol), polypropylene glycol), poly(butylene glycol), poly(methylmethacrylate), poly(dimethylsiloxane), poly(vinylalcohol), poly(styrene), poly(maleic anhydride), poly(ethylmethacrylate), poly(isobutylmethacrylate), poly(methacrylate), poly(butylmethacrylate), poly(n-butylmethacrylate), poly(vinyl butyrate), poly(vinyl chloride), polysiloxane, and mixtures thereof. The polymers can be random, block, or alternating copolymers. In some embodiments, the polymer is a co-polymer that is made from two or more different monomers, such as the monomers that make the polymers described above. Examples of co-polymers include, but are not limited to polyethers, polyesters, polyamides, acrylics, and polystyrenes. The co-polymer can be alternating monomers, random, or block. Examples include a polyether of alternating or block PEO, PPO groups. Examples of acidic groups include, but are not limited to, carboxylic acids, sulfonic acids, sulfonic acids, phosphonic acids, phosphate esters, maleic anhydrides, and succinic anhydride. In some embodiments, the dispersive additive comprises a group selected from phosphonate, phosphate, phosphite, phosphine, and phosphate ester, such as a phosphate, phosphite, and phosphonic acid. In some embodiments, the acidic group has been converted into a salt.

In some instances, the pigments described herein can be chosen and/or modified to be similar enough (e.g., by surface treatment) such that a single dispersant can be used. In other instances, where the pigments are different, but compatible, two or more different dispersants can be used.

In some instances the cationic polymer may also act as a dispersant for the pigments.

Pigments are dispersed through the use of high shear mixing; for example through use to the appropriate ball mill, ultra high pressure homogenizer or other system known by those skilled in the art of pigment dispersion.

G. Surface Treatment

The pigment microparticles can be subjected to a surface treatment prior to suspending the particles in the carrier medium such as aqueous medium. The surface treatment aims for changing surface properties to improve wetting, dispersing, and stabilizing the microparticles in the carrier medium.

The dispersant, either added to the medium or provided as coating, facilitates wetting of the microparticles, dispersing of the microparticles in the medium, and stabilizing of the microparticles in the medium.

The wetting includes replacing of materials, such as air, adsorbed on the surface of the pigment microparticles and inside of agglomerates of the microparticles by the medium. Typically, a complete wetting of the individual microparticles is desired to singularize the particles and to break off agglomerates formed by microparticles adhering to each other.

After wetting, the microparticles can be subjected to de-aggregate and de-agglomerate step, generally referred to as dispersing step. The dispersing step typically includes the impact of mechanical forces such as shear to singularize the microparticles. In addition to that, the microparticles can be broken into even smaller microparticles using, for example, roller mills, high speed mixers, and pebble mills.

During wetting and dispersing, the exposed total surface area of the microparticles increases which is wetted by the dispersant. The amount of the dispersant may be gradually increased during dispersing to account for the increased surface area.

The dispersant also functions as de-flocculation agent keeping the dispersed microparticles in a dispersed state and prevent that they flocculate to form loose aggregates. This stabilization is also needed for long term storage purposes. Different type of stabilization such as electrostatic stabilization and steric stabilization are possible, and the type of dispersant is selected in view of the medium and the material of the microparticles.

The dispersant can be grouped into two main groups: polymeric dispersants and surfactants. Polymeric dispersants stabilize the microparticles mainly through steric stabilization. Polymeric dispersants include specific anchorages groups for bonding to the surface of the microparticles and a polymeric chains. Surfactants are—in comparison to poylmeric dispersants—low molecular weight dispersing agents having a hydrophobic and a hydrophilic portion. Widely used surfactants for dispersing pigment microparticles are—without being limited thereto—fatty acid derivatives, phosphate esters, sodium polyacrylates/polyacrylic acid, acetylen diols, soya lecithin.

The dispersant may be added to a dry powder of the pigment particles when the particles are milled to a desired size. During milling, or any other suitable technique to singulate the pigment particles or to break them into smaller part, the dispersant comes in contact with and adheres to the surface of the microparticles. Freshly generated microparticle surface during milling will be coated by the dispersant so that, after milling, the microparticles with a coating formed by the dispersant are provided.

The coating with the dispersant can also be carried out in a liquid carrier medium to which the dispersant is added. The microparticles can also be milled in the liquid carrier.

H. Optional Components

Optional components of the composition include suspending agents, leveling agents and viscosity control agents. The suspending agents help maintain the pigment particles in dispersed condition and minimize or negate their agglomeration. Suspending agents include fatty acid esters of polyols such as polyethylene glycol and polypropylene glycol. These are similar to plasticizers and function in similar fashion to allow pigment particles to "slip" by each other without retarding or binding interaction. They act as grease in this fashion. Additionally, suspending agents in part participate in promoting the stable dispersion of the pigment particles and avoid settling. The pigment particles on average are small enough so that Brownian movement participates in maintaining their dispersion. The carboxylic acid polymer also participates through its solubilization or interaction with the pigment particles and with the medium. The suspending agents provide another factor for maintaining the stable dispersion. They not only provide the "grease" to facilitate Brownian movement but also in part stabilize through interaction as emulsifiers of the pigment particles in the medium.

The hair coloring composition embodiments in accordance with the present invention can also optionally contain at least one adjuvant, chosen, for example, from reducing agents, fatty substances, softeners, antifoams, moisturizers, UV-screening agents, mineral colloids, peptizers, solubilizers, fragrances, anionic, cationic, nonionic, or amphoteric surfactants, proteins, vitamins, propellants, oxyethylenated or non-oxyethylenated waxes, paraffins, $C_{10}$-$C_{30}$ fatty acids such as stearic acid or lauric acid, and $C_{10}$-$C_{30}$ fatty amides such as lauric diethanolamide.

The hair coloring composition embodiments in accordance with the present invention can further optionally contain one or more additives, including, but not limited to, antioxidants (e.g., phenolics, secondary amines, phosphites, thioesters, and combinations thereof), crosslinking agents, reactive diluents (e.g., low molecular weight mono- or di-functional, non-aromatic, (meth)acrylate monomers such as 1,6-hexanediol di(meth)acrylate, tripropylene glycol di(meth)acrylate, isobornyl(meth)acrylate, 2(2-ethoxy-ethoxy)ethyl(meth)acrylate, n-vinyl formamide, tetrahydrofurfuryl(meth)acrylate, polyethylene glycol di(meth)acrylate, tripropylene glycol di(meth)acrylate, neopentyl glycol dialkoxy di(meth)acrylate, polyethyleneglycol di(meth)acrylate, and mixtures thereof), non-reactive diluents (e.g., ethylene glycol, di(ethylene glycol), tetra(ethylene glycol), glycerol, 1,5-pentanediol, ethylene glycol monomethyl ether, ethylene glycol dimethyl ether, triethylene glycol monomethyl ether, 2-ethoxyethanol, solketal, benzonitrile, hexamethylphosphoramide, 2-N-methylpyrrolidinone and N,N-dimethylformamide); dyes, fillers (e.g., silica; carbon black; clay; titanium dioxide; silicates of aluminum, magnesium, calcium, sodium, potassium and mixtures thereof; carbonates of calcium, magnesium and mixtures thereof; oxides of silicon, calcium, zinc, iron, titanium, and aluminum; sulfates of calcium, barium, and lead; alumina trihydrate; magnesium hydroxide and mixtures thereof), plasticizers (e.g., petroleum oils such as ASTM D2226 aromatic oils; paraffinic and naphthenic oils; polyalkylbenzene oils; organic acid monoesters such as alkyl and alkoxyalkyl oleates and stearates; organic acid diesters such as dialkyl, dialkoxyalkyl, and alkyl aryl phthalates, terephthalates, sebacates, adipates, and glutarates; glycol diesters such as tri-, tetra-, and polyethylene glycol dialkanoates; trialkyl trimellitates; trialkyl, trialkoxyalkyl, alkyl diaryl, and biaryl phosphates; chlorinated paraffin oils; coumarone-indene resins; pine tars; vegetable oils such as castor, tall, rapeseed, and soybean oils and esters and epoxidized derivatives thereof; esters of dibasic acids (or their anhydrides) with monohydric alcohols such as o-phthalates, adipates and benzoates; and the like and combinations thereof), processing aids, ultraviolet stabilizers (e.g., a hindered amine, an o-hydroxy-phenylbenzotriazole, a 2-hydroxy-4-alkoxybenzophenone, a salicylate, a cyanoacrylate, a nickel chelate, a benzylidene malonate, oxalanilide, and combinations thereof), and combinations thereof.

I. Solids Content

Embodiments of the hair coloring composition include solids and liquids. The solids comprise any substance or material of the hair coloring composition that in a form uncombined with any other material, solvent, liquid or substance is has a solid physical form at ambient conditions. Included at least are the carboxylic acid polymer and the pigment microparticles of the hair coloring composition. The medium, in contrast is a liquid and functions as a solvent and/or a liquid in which solid particles are dispersed. The optional components as well as the plasticizer, dispersing agent, surface treatment agent, cross linking agent and other materials added to the medium, if any, are included in the solids content as long as they remain with the carboxylic acid polymer and pigment microparticles following application and setting of the hair coloring composition as a coating on strands of human hair. This includes substances that ordinarily would be regarded as liquids because they would remain in the coating on strands of hair. The solids content of the hair coloring composition may range from about 1 wt % to about 40 wt % relative to the total weight of the composition. A preferred solids content ranges from about 2 wt % to about 30 wt % and another preferred solids content ranges from about 4 wt % to about 20 wt % relative to the total weight of the composition. An especially preferred solids content range is about 4 wt % to about 10 wt % with contents of about 5 wt %, about 6 wt %, about 7 wt %, about 8 wt %, about 9 wt % and about 10 wt % being more especially preferred.

Testing the Flexibility of a Dual Component Coating

The coating produced by applying the colored hair composition to keratin fibers such as human hair must easily expand, contract and flex without flaking, peeling, shedding or detaching. Hair is frequently moving and is highly flexible. The coating needs to mimic these properties of hair. This reduces the chance of the coating from being damaged or cracked which would reduce its wash resistance. From this viewpoint, the coating elongation of the polymer(s) used within the composition is in the range of about 25% to about 1200%, in the range of about 35% to about 1200%, in the range of about 60% to about 1200%, or in the range of about 70% to about 1200%.

Here, the coating elongation of the dual component coating is measured as follows. Firstly, compositions A and B are sequentially coated and dried on a polytetrafluoroethylene sheet such that the film thickness after drying becomes 500 µm, dried at normal temperature (20° C.) and at normal pressure (65% RH) for 15 hours, and further dried at 80° C. for 6 hours and at 120° C. for 20 minutes, and then is peeled off from the sheet to form a polymer film. Further, the coating elongation of the obtained dual film is measured using a tension tester at a measurement temperature of 20° C. and Measurement speed of 200 mm/mm. The measurement of the coating elongation is performed by elongating the film and measuring the length of the coating film elongated before being damaged, and the ratio thereof is represented as the coating elongation as a percentage. In addition, as the tension tester, for example, a tensilon universal tester RTC-1225A (trade name, Orientec Co., Ltd.) or a tester equivalent to the tensilon universal tester can be used.

With the film prepared above, it can also be tested for optical density to check that the dual polymer film does not itself alter the hair appearance of the hair too significantly.

Further the dual polymer preferably can have a glass transition point (Tg) as described above so that it is possible to prevent the colored coating from being damaged or cracked and to secure washing and friction fastness.

The dual polymer coating can have a surface energy between about 20 and about 50 mJ m$^{-2}$. The dual polymer coating preferably has high transmission, to ensure that it does not interfere with the optics of the hair color. The polymers preferably have a refractive index between 1.4 and 1.6.

Method for Coating Hair

The hair coloring composition aspect of the present invention can be applied to keratin fibers to form a dual coating of the first layer of cationic polymer with pigment particles and a second layer of anionic polymer optionally in situ cross linked. This aspect of the invention concerns a method for coloring keratin fibers and comprises applying embodiments of one or more hair coloring compositions for a time sufficient to deposit an effective colored coating on each keratin fiber. A somewhat to substantially overall distribution of the coating on the length and circumference of each fiber is produced.

To accomplish this aspect, embodiments of the hair coloring composition comprising a first composition A of the amine polymer in un-neutralized or neutralized form in the medium with dispersed the pigment particles and other optional components is applied to the hair by brushing, painting, spraying, atomizing, squeezing, printing, rubbing massaging or in some manner coating the hair strands with the composition A embodiment. Following application of a composition A embodiment to the hair strands, the composition A is set preferably by warming with blown warm air from a hair dryer or similarly treated to remove the medium. Next embodiments of the hair coloring composition comprising the second composition B of the carboxylic acid polymer in preferably neutralized form in aqueous medium is applied to the hair already coated with dried composition A, by brushing, painting, spraying, atomizing, squeezing, printing, rubbing massaging or in some manner coating the hair strands with the composition B embodiment. Following application of a composition B embodiment to the hair strands, the composition B is set preferably by warming with blown warm air from a hair dryer or similarly treated to remove the medium. If in situ cross linking agent is present, the warm air will initiate cross linking of the carboxylic acid polymer and cross linking agent and if present, remove the volatile base. The setting enables the ionic interaction to take place between the cationic polymer and the anionic polymer thereby producing electrostatic bonding between carboxyl anions and ammonium cations and providing adherence to the dual layer coating. If cross linking is included, the setting also enables partial cross linking of the carboxyl polymer but because of the low to low/moderate extent of cross linking does not negate the electrostatic bonding between the polymers of the dual layers.

The dual coating of carboxylate polymer and ammonium polymer results from the use of water-soluble carboxylic acid polymer and water soluble amine polymer (i.e., carboxylic acid polymer or copolymer) in compositions A and B. While the polymer or copolymer is hydrophilic before application, the electrostatic interaction between polymer layers provides a dual adherent coating that enables it to resist for a time destruction by washing with dilute mixtures of soap and water or shampoo and water. Color fastness is developed so that washing with dilute aqueous soap solution or dilute aqueous shampoo will not substantially remove the coating, but the coating can be facilely removed by use of a transformation trigger. The properties of the coating include wash-fastness, flexibility, adhesion, abrasion resistance and remanence which are due at least in part to the electrostatic interaction of the carboxylic acid polymer and the amine polymer and their interpolymer entwining, non-covalent cross linking, ionic and electrostatic intermolecular interaction, covalent and/or non-covalent cross-linking, dipole interaction and lipophilic interaction of neutral moieties of the polymers.

Selection of the particular carboxylic acid polymer and amine polymer for an embodiment of the hair coloring composition can be made on the basis of their properties as a solid lattice and polymer interaction. Such properties include the flexibility, the hardness, the adhesion, the remanence, the resistance to water or to other chemical compounds, and the abrasion resistance. It is also possible to take advantage of the more versatile properties of block polymers (polymers comprising at least two distinct polymer segments), grafted polymers (polymers containing a polymeric side chain grafted onto the homopolymer or copolymer backbone), or random copolymers (polymers comprising at least two different monomers). In the block copolymers, for example, the amount of hard and soft blocks has a significant impact on the properties of the polymer.

The hair coloring compositions in accordance with the present disclosure can have a viscosity that can be controlled to enable compositions A and B to be applied to the hair using either a brush and bowl or a bottle, but with sufficient rheology such that it does not drip and run from the hair onto the face or body.

The hair coloring compositions can be utilized in concentrated form or in serial dilutions, to provide for a consistent color results substantially along the entire length of the keratin fibers.

The aspect of coloring mammalian or synthetic keratin fibers with a hair coloring composition as described above includes a method for this coloring. The method comprises applying the above-described hair coloring composition to keratin fibers an effective coloring amount of the composition of medium with carboxylic acid polymer, pigment microparticles and optional additional components; and setting the hair coloring composition by removing or otherwise eliminating the medium (e.g., by drying the composition).

As described above, if a cross linker is present in composition B, the setting step during application of composition B of the hair coloring composition to the hair facilitates the cross-linking.

During the setting/drying step, color distribution can be facilitated by concurrently moving and/or stroking the hair with an interdigitating device. Interdigitating devices include a comb or brush. The interdigitating device needs to be pulled substantially along the hair strands from root to tip. It can be pulled through at a rate of 0.1 cm $s^{-1}$ to 50 cm $s^{-1}$ or at a rate between 0.5 cm $s^{-1}$ to 20 cm $s^{-1}$.

The hair coloring composition is applied to the mammalian or synthetic keratin fibers in any suitable way including spraying the hair coloring composition, massaging the keratin fibers by hand, after applying the hair coloring composition to the hand or by combing, brushing or otherwise applying the hair coloring composition throughout the mammalian or synthetic keratin fibers.

Unlike current hair coloring approaches that use dyes, the color with the hair coloring compositions described herein occurs on the surface of the hair strands. Current dye ased approaches do provide the head of hair with some color variation, as the strands are not identical, and some of these differences are preserved after coloring. There are also differences root to tip which also helps to provide some variation. Using a pigment based surface coloring system such as that of the present invention, the variation of the underlying hair can be substantially removed, leading to a more homogeneous color result. This color result can be a more homogenous application of color. To obtain a somewhat non-homogeneous application of color that tends toward a more natural look, the user can apply the inventive hair coloring composition by any of several techniques.

The methods by which the hair coloring compositions described herein are applied can be modified, such that the user applies the product in one region of the hair, and then apply a diluted version in another region of the hair. The dilution formula is specially chosen to be compatible with the colorant formulation and reduces the coloring strength, while maintaining the longevity of the color result. This can effectively be a "blank" formulation, which contains broadly the same materials as the coloring formulation, but with lower or no pigments present. When diluted the ratio of the diluent to colorant can be between about 10:1 and about 1:10, about 8:1 and about 1:2 or about 5:1 and about 1:1.

Alternatively, the amount of hair coloring composition applied can be altered in different regions of the hair, for example half the product is applied in the lengths of the hair, leading to a less colorful result. The difference in amounts applied in one region of the hair versus another can be between about 4:1 and about 1:4 or about 2:1 and about 1:2.

Alternatively a combination of this approaches may be used to deliver the target color variation.

When the foregoing techniques are not possible to be applied, rather than apply a single hair color, it may be possible to apply two or more hair colors to different regions of the hair. When this is done, the different hair colors preferably provide complimentary colors so as to develop an attractive result. The difference in colors that can be used, based on the end result on hair tresses are as follows. As described within the CIELABCH system:

Color 1 (LCH) versus Color 2 (LCH)
Color 1 L-15<Color 2 L<Color 1 L+15
0 or Color 1 C-10<Color 2 C<Color 1 C+10
Color 1 H-45<Color 2 H<Color 1 H+45

Those skilled in the art of color measurements will know how to interpret difference in hue angles, H, when they extend from low positive values to those near to 360 degrees due to the circular nature of the hue angle.

The method for use of the hair coloring composition in accordance with the present invention can occur during any suitable period. The period of application can be from about 10 to 45 minutes, but in any event a period that is sufficiently long to permit the coating of pigment microparticles to coat and adhere or bind to each separate keratin fiber, substantially along the entire length of each keratin fiber. The resultant is keratin fibers having a color and permanence that is at least equivalent to the color resulting from oxidative hair color, except under much milder conditions.

The composition A component of the hair coloring compositions described herein can be prepared by the manufacturer as a full shade, e.g., one that is ready to apply to the hair, and then shipped as a discrete unit to the user. The user may need to re-blend composition A of the hair coloring composition prior to application to ensure that the hair coloring composition delivers the optimum performance. Such re-blending can require shaking composition A of the hair coloring composition for about 1 to about 120 seconds or from about 3 to about 60 seconds, Reblending may also be performed by stirring composition A of the hair coloring composition prior to use. This may occur for about 1 to about 120 seconds or from about 3 to about 60 seconds. Although composition A of the hair coloring compositions according to the present invention are designed to provide stable suspensions of the pigment particles, the re-blending to agitate the particles and resuspend them in a substantially uniform distribution is desirable.

Alternatively, the hair coloring composition can be made on demand from a series of discrete formulations and mixed ready for use. Each hair coloring composition would need to be designed such that the combinations of two or more composition A's of the hair coloring compositions produce readily mixable hair coloring compositions with sufficient stability to be used. For example, at least four composition A's of the hair coloring compositions can be made available for blending, at least 5 hair coloring compositions and even at least 6 hair coloring compositions. Additional composition A may also be used to impart other signals into the product, for example modifying the rheology, changing the perfume, altering the shine or hair feel properties.

Multiple composition A's comprising different pigments can be blended together prior to application to the keratin fibers. Such blending can be done in a manner so as to apply a plurality of complementary surface colors to the keratin fibers.

Another aspect of the present invention is directed to a method for multiple coloring of mammalian or synthetic keratin fibers, the method comprising:

applying a first composition A hair coloring composition in accordance with the foregoing description so that the composition is distributed substantially along the entire length of each keratin fiber for a time sufficient to deposit an effective coloring amount of first pigment microparticles on the mammalian or synthetic keratin fibers;

applying a second composition A hair coloring composition in accordance with the foregoing description so that the second composition A is distributed substantially along the entire length of each keratin fiber for a time sufficient to deposit an effective coloring amount of second pigment microparticles on the first pigment microparticles; and setting the hair coloring composition.

The first composition A hair coloring composition can function to enhance the adhesion between the hair and the second hair coloring composition since the first composition A hair coloring composition positioned on the hair more or less functions as and intertwining element between the hair and the second hair coloring composition. The first composition A hair coloring composition can be applied immediately prior to applying the second composition A hair coloring composition; at least 1 hour prior to applying the second hair coloring composition; at least 24 hours prior to applying the second composition A hair coloring composition; or at least 10 days prior to applying the second composition A hair coloring composition, or at least one month prior to applying the second composition A hair coloring composition.

The hair coloring compositions can include multiple layers, including at least one layer comprising pigment microparticles comprising at least a medium containing a dispersion of at least one pigment and a dissolved amine polymer. Optional additional solvents, wetting agents dispersing agent, and plasticizer may be included.

The coating of pigment microparticles comprising at least one pigment in a coating of amine polymer can be adhered to the hair utilizing a coating having a total thickness at any given point along the hair fiber of less than about 5 µm, preferably less than about 2 µm as measured using a scanning electron microscope (SEM). To make such measurements, a coated hair sample can be embedded in a suitable resin, and then sectioned root to tip using techniques known to those skilled in the art of scanning electron microscopy. The thickness of the layer on the surface can then be assessed along the line of cuticles over a length of at least 100 µm. The thickness of layer is determined by averaging 10 points evenly spaced over the section of interest.

As described above, application of the hair coloring composition to sections of a hair strand can be varied. In addition to varying the concentration of the pigment microparticles and optional coloring agent, different shades and/or colors of hair coloring composition A can be applied to different sections of a strand of hair or a group of strands of hair. For example, the hair roots, mid sections and tips sometimes or often have different shades of color in their natural condition. This variation can be mimicked, altered or covered through use of differing shades or colors of the hair coloring composition. Roots, for example can be covered with a lighter shade and the tips can be covered with a darker shade to produce a two tone variation of the hair. Application to the hair of the first hair coloring composition A followed by stripping the composition A from the hair mid sections and ends followed by setting the remaining composition on the hair roots will provide a first hair color coating on the roots. The mid-sections and tips can be dipped or brush applied with a second hair coloring composition A to complete the two color or two tone treatment. The use of multiple hair coloring composition A's to produce multiple coatings on the hair can provide overlapping, sequential or coterminous coatings on the hair according to typical and routine techniques for applying multiple versions of hair color practiced by professional hair salons. After completing the multiple composition A applications, composition B can be applied and processed as described above to provide the completed multiple color hair composition.

Post Treatment

A post treatment composition can be applied after treating hair with the hair coloring compositions described herein. This can be applied either directly after the coloring composition without and intermediate drying step, or after the coloring composition has been dried. The post treatment can be either single application or multiple application across time. The post treatment can be used to improve one or more of: feel, resistance to shampoo/conditioner/water washing treatments, and shine of the hair. Nonlimiting examples of materials used to improve the feel are those which impart lubricity to the hair fibres and/or help the hair fibers separate during the drying steps, for example silicones, silicone polyethers, silicone polyglucose, polyisobutene, copolymers of ethylene and propylene oxide, and commonly used cosmetic oils and waxes. Nonlimiting examples of materials used to improve shampoo wash resistance are crosslinking materials (as described herein in the crosslinker section) or materials which act as a 'sacrificial layer' for example polymeric silicones and their copolymers, silicone resins, cosmetics oils and waxes. Nonlimiting examples of materials used to improve the shine of hair (meaning a decrease of the full width at half maximum parameter of the specular reflection curve as measured by a goniophotometer) are those materials which form a smooth film above the previously applied pigment polymer composite on the hair. In general, any cosmetically known film forming material can be used, but preferred are materials such as polymeric silicones and polycationic materials.

Removal of Color Coating

The colored coating of the keratin fibers made according to the foregoing aspects of the invention can be removed substantially in total due to at least the non-penetrance of the pigments into the keratin fiber. The surface coloration can be removed substantially in total by, e.g., dissolving the coating of carboxylic acid polymer, olefinic ester or polar functionalized silicone holding the pigment microparticles on the exterior surface of the keratin fiber.

The surface coloration can be removed substantially in total by dissolving the coating adhered to the exterior surface of the keratin fiber. This removal is accomplished through use of a trigger agent. While dilute mixtures of soap and water or shampoo and water will not readily dissolve the coating, use of a trigger agent which will significantly penetrate the interdependent polymer lattice and change the microenvironment especially its pH.

Changing the pH can have a dramatic impact on the properties of the polymer film which is adhered to the surface. A soluble base acting as a trigger agent to interact preferentially with the carboxylic acid groups and enable the conjugate acid to be readily soluble in a mixture of water and organic solvent will facilely remove the coating. Such bases include amino alcohols such as dimethylaminoethanol (dimethylethanolamine, DMEA), dimethylaminopropanol, and similar amino alkanol agents such as monoethanolamine, diethanolamine and triethanolamine and ammonia. Other bases such as NaOH and CaOH can also be used. A warm aqueous solution of the trigger agent is useful in this regard. The concentration of the trigger agent in aqueous solution optionally with an alcohol or ketone organic solvent such as methanol, ethanol, methyl ethyl ketone and the like may range from about 0.1% to about 15% by weight, preferably about 0.5% to about 10% by weight, more preferably about 1% to about 7.5% by weight relative to the total weight of the removal solution. While an aqueous alcoholic solution of an alkali metal hydroxide will also remove the coating, it is too harsh for application to mammalian skin, especially human skin.

The hair coloring removal composition can be applied to the mammalian or synthetic keratin fibers in any suitable way including spraying the hair coloring composition, massaging the keratin fibers by hand, after applying the hair coloring composition to the hand or by combing the hair coloring composition through the mammalian or synthetic keratin fibers. When the product is applied to the hair, the product can be physically distributed to cover all of the hair, and the action of distributing the product around the hair aids in the removal process.

A process that enables the rapid change of hair color requires the following steps. Application of a pigment based hair colorant compositions A and B to the hair, with an optional pre-treatment and post treatment. Leaving the color on the hair for one day, preferably for more than one day. Application of a trigger composition to remove the hair color, followed by rinsing and drying the hair. The subsequent application of a hair coloring composition A and B to the hair, with an optional pre-treatment and post treatment will again color the hair with no untoward after effects.

The temporary but lasting quality of the hair coloring composition applied to hair and set as the coating on hair can be determined by measurements indicating substantially permanent pigment lastingness. Substantially permanent pigment lastingness generally is indicated when the color of the colored hair fibers changes less than 50%, less than 40%, less than 30%, less than 20%, less than 10% after the colored hair fibers are processed through a 12-cycle rinse study. One cycle is defined as two shampoo treatments followed by a conditioning treatment. Two hair tresses (Kerling, Natural White special quality) are measured for their initial color and then colored according to the current disclosure. The color of the hair is again measured. For washing, the hair is wetted for 30 seconds, a shampoo is applied (0.1 per gram of hair) and lathered into the hair for 30 seconds, followed by rinsing for 30 seconds, a further dose of shampoo is applied (0.1 g per gram of hair) and lathered for 30 seconds, followed by rinsing for 30 seconds a conditioner is then applied (0.1 g per gram of hair) for 30 seconds and then rinsed for 30 seconds. The hair is then blow dried for 2 minutes. The water is set to flow at 4 L/min and with a temperature of 37 2° C. This completes one wash cycle which is then repeated as additional 11 times. A final color measurement is performed. Color data is collected before coloring, after coloring and after washing using a Minolta spectrophotometer CM-2600d. The lastingness is calculated as follows. The CIELAB $dE_{76}$(fade) is calculated between the after coloring and after washing.

This is assigned as the amount of color lost. The amount of color provided by the given formulation is the CIELAB $dE_{76}$(color) between the before coloring and after coloring. The amount of fade is then computed as FADE=$dE_{76}$(fade)

dE$_{76}$(color)*100. The substantially permanent lastingness is reversed at more than 80%, preferable more than 90% even more preferably close to 100% FADE. One way that the substantially permanent lastingness can be reversed at or close to 100% of removal of perceived color change is by using a solvent or combination of solvents to remove the pigment microparticles comprising at least one pigment from the keratin fibers.

Damage caused to the hair by application of the hair coloring composition and removal of the resulting coating can be assessed by FT-IR (Fourier Transform Infrared) method, which has been established to be suitable for studying the effects of oxidative treatments on hair (Strassburger, J., J. Soc. Cosmet Chem., 36, 61-74 (1985); Joy, M. & Lewis, D. M., Int. J. Cosmet. Sci., 13, 249-261 (1991); Signori, V. and Lewis, D. M., Int. J. Cosmet. Sci, 19, 1-13 (1997)). In particular, these authors have shown that the method is suitable for quantifying the amount of cysteic acid that is produced from the oxidation of cystine. In general, the oxidation of cystine is thought to be a suitable marker by which to monitor the overall oxidation of the keratinous part of the fiber. Net, the measurement of cysteic acid units by FT-IR is commonly used to study the effects of oxidative treatments or environmental oxidation upon keratin protein containing fibers such as hair and wool.

Signori and Lewis (D. M., Int. J. Cosmet. Sci., 19, 1-13 (1997)) have shown that FT-IR using a diamond Attenuated Total Internal Reflection (ATR) cell is a sensitive and reproducible way of measuring the cysteic acid content of single fibers and bundles. They have shown that this technique is more suitable than using the FT-IR method in simple transmission or microscope modes. They have also shown that the diamond cell ATR was significantly more sensitive and reproducible than the ZnSE cell. Hence, the method that we have employed to measure the cysteic acid content of multiple fiber bundles and full hair switches, is based upon the FTIR diamond cell ATR method employed by Signori and Lewis (1997). The detailed description of the method used for testing the different damage inhibitors follows thereafter:

A Perkin Elmer Spectrum® 1 Fourier Transform Infrared (FTIR) system equipped with a diamond Attenuated Total Internal Reflection (ATR) cell was used to measure the cysteic acid concentration in mammalian or synthetic hair. In this method, hairswitches of various sizes and colors can be used. The switches were platted (–1 plait per cm) in order to minimize variations in surface area of contact between readings. The Oxidative hair Treatment Protocol described above was repeated for 5 cycles to mimic the behavior of hair after repeated bleaching cycles. Following this treatment, four readings per switch were taken (⅓ and ⅔s down the switch on both sides), and an average calculated. Backgrounds were collected every 4 readings, and an ATR cell pressure of 1 N/m was employed. The cell was cleaned with ethanol between each reading, and a contamination check performed using the monitor ratio mode of the instrument. As prescribed by Signori & Lewis in 1997, a normalized double derivative analysis routine was used. The original spectra were initially converted to absorbance, before being normalized to the 1450 cm$^{-1}$ band (the characteristic and invariant protein CH$_2$ stretch). This normalized absorbance was then twice derivatised using a 13 point averaging. The value of the 1450 cm$^{-1}$ normalized 2nd derivative of the absorbance at 1040 cm$^{-1}$ was taken as the relative concentration of cysteic acid. This figure was multiplied by –1×10$^{-4}$ to recast it into suitable units. It was found that virgin mammalian or synthetic hair produced a value of around 20 cysteic acid units, and heavily oxidized hair produced values of around 170. The following instrumental conditions were employed:

Spectral Resolution—4 cm$^{-1}$
Data interval—0.7 cm$^{-1}$
Mirror Scan Speed—0.2 cm s$^{-1}$
Number of Background Scans—20
Number of Sample Scans—20
Scan Range—4000 cm$^{-1}$ to 600 cm$^{-1}$ When the compositions of the current invention can be applied to the hair and then removed there can be a non-significant change to the level of oxidative damage to the hair, whereas with conventional oxidative colorants there can be a large increase in the measured oxidative damage.

The instant disclosure is not limited in scope by the specific compositions and methods described herein, since these embodiments are intended as illustration of several aspects of the disclosure. Any equivalents are intended to be within the scope of this disclosure. Indeed, various modifications in addition to those shown and described herein can be within the grasp of those with ordinary skill in the art. Such modifications are also intended to fall within the scope of the appended claims.

Also contemplated herein are hair coloring compositions having a given color area defined by color coordinates (a*, b*) in the color space represented by the L*a*b* color system, which can be divided into a plurality of color areas. Each of the plurality of colors obtained from the area surrounding a given set of hair fibers is judged to belong to which color area of the colored area of a certain color. The number of colors judged for each color area is counted, and the color of the color area with the largest number of colors is selected as a representative color of the area surrounding a given set of hair fibers. The compositions are capable of delivering colors on hair (test method herein for fade) such that the results colors lie within the range of about 18<L<about 81, about –2<a<about 45, and about –13<b<about 70.

Also contemplated herein are hair coloring compositions that do not change the underlying hair color, but instead change some other feature of the hair including shine (e.g., making it shinier or matte), the thickness of the hair and/or the feel of the hair.

When the color is removed from the hair, the waste water/composition can be treated to remove the pigments from the waste water effluent system. This can be achieved by filtration, or through cyclone technology, where the density differences are used to force the pigments to the settle, and the water to pass through.

GENERAL EXAMPLE

Examples 1 to 9

The following is a non-limiting example of the method of the present invention. The representative example is given solely for the purpose of illustration and is not to be construed as limitations of the present invention, as many variations thereof are possible without departing from the spirit and scope of the invention, which would be recognized by one of ordinary skill in the art.

The hair swatches are provided from Kerling International Haarfabrik GmbH, Backnang, Germany.

In a first step, a composition A containing a cationic polymer A, and optionally a selected Pigment, a polymer solvent and a pigment dispersant (in the respective concentration to arrive at 100%) can be prepared. This composition can be smoothly mixed with a brush and applied on the hair swatch. The total amount is 1 g per hair swatch. After the hair swatch is fully covered with the Polymer/Pigment composition the hair swatch can be left at room temperature for 5 min. The hair swatch can be dried smoothly with a towel and a solution of Composition B (anionic polymer and optionally pigment in polymersolvent (C. medium) and pigmentdispersant) can be applied on top of the hair swatch. The hair swatch can be again left for a residence time of 15 min. Afterwards the hair swatch can be dried with the blow dryer to set the polymer on the hair while combing until it is dry to the touch and the strands are individualised.

The hair tresses can be left for 24 hours at room temperature and different pigments and different polymer combinations can be compared after the final tresses can be repeatedly washed for multiple times with a normal shampoo and may be examined for color intensity.

|  | Composition A | | Composition B | |
| --- | --- | --- | --- | --- |
|  | Pigment A | Cationic Polymer A | Anionic Polymer B | Pigment B |
| Ex 1-3: 1 = Pigment in A 2 = Pigment in B 3 Pigment in A + B | 1-5% Violet 19; Clariant | 0.5%-5% FLOQUAT ™ FL 45 C, SNF FLoerger | 0.2%-5% Covacryl P12; Sensient | 1-5% Violet 19; Clariant |
| Ex 4-6: 4 = Pigment in A 5 = Pigment in B 6 Pigment in A + B | 1-2% Pigment Blue 15; Clariant | 0.5%-5% LUPASOL SK-BASF | 0.1%-2% Acrysol 162A; Dow Corning | 1-2% Pigment Blue 15; Clariant |
| Ex 7-9 7 = Pigment in A 8 = Pigment in B 9 Pigment in A + B | 1-4% Pigment Yellow 104 (CI 15985), CAS# 2783-94-0 | 0.5%-5% FLOQUAT ™ FL 45 C, SNF FLoerger | 0.01%-5% Avalure AC 120 - Lubrizol | 1-4% Pigment Yellow 104 (CI 15985), CAS# 2783-94-0 |
| Example for Polymersolvent as defined as under the C. medium section: | | e.g. water or polar or non polar organic solvents | | |
| Example for Pigment dispersants as defined under dispersant section | | e.g. Solsperse W-100; LUBRIZOL | | |

Summary Statements

The inventions, examples and results described and claimed herein may have attributes and embodiments include, but not limited to, those set forth or described or referenced in this application.

All patents, publications, scientific articles, web sites and other documents and ministerial references or mentioned herein are indicative of the levels of skill of those skilled in the art to which the invention pertains, and each such referenced document and material is hereby incorporated by reference to the same extent as if it had been incorporated verbatim and set forth in its entirety herein. The right is reserved to physically incorporate into this specification any and all materials and information from any such patent, publication, scientific article, web site, electronically available information, text book or other referenced material or document.

The written description of this patent application includes all claims. All claims including all original claims are hereby incorporated by reference in their entirety into the written description portion of the specification and the right is reserved to physically incorporated into the written description or any other portion of the application any and all such claims. Thus, for example, under no circumstances may the patent be interpreted as allegedly not providing a written description for a claim on the assertion that the precise wording of the claim is not set forth in haec verba in written description portion of the patent.

While the invention has been described in conjunction with the detailed description thereof, the foregoing description is intended to illustrate and not limit the scope of the invention, which is defined by the scope of the appended claims. Thus, from the foregoing, it will be appreciated that, although specific nonlimiting embodiments of the invention have been described herein for the purpose of illustration, various modifications may be made without deviating from the scope of the invention. Other aspects, advantages, and modifications are within the scope of the following claims and the present invention is not limited except as by the appended claims.

What is claimed is:

1. A hair coloring composition comprising:
  a pretreatment composition comprising a second cationic polymer and an aqueous medium with no pigment particles,
  a first composition A comprising a first cationic polymer and an aqueous medium,
  a second composition B comprising an anionic polymer and an aqueous medium,
  and pigment particles contained in the first composition A or contained in the second composition B or contained in a combination thereof;
  wherein the pretreatment, first and second compositions are maintained in separate containers; and
  the first and second cationic polymers are the same or different.

2. The hair coloring composition of claim 1, wherein the first and second cationic polymers independently are an olefinic polymer having pendant amine groups, an olefinic polymer having nitrogen atoms in the polymer chain and optionally having pendant amine groups or an amino silicone polymer.

3. The hair coloring composition of claim 1, wherein the anionic polymer of composition B is a carboxylic acid polymer comprising an olefinic carboxylic acid homopolymer or copolymer or terpolymer, an olefinic carboxylate ester polymer with pendant carboxylic acid groups, an olefinic polymer with pendant carboxylic acid groups, a cellulosic polymer with carboxyl and/or sulfonic acid groups, an olefinic polymer with pendant aromatic sulfonate groups, gamma carrageenan, dextran sulfate salt, or an alginic acid salt.

4. The hair coloring composition of claim 3, wherein the olefinic carboxylic acid monomeric unit and/or olefinic carboxylate ester monomeric unit and/or the olefinic monomeric unit is alkenoic or alkendioic acid of 3 to 10 carbons, (meth)acrylic acid, maleic acid, fumaric acid, itaconic acid, crotonic acid, pentenoic acid; alkadienoic acid of 5 to 12 carbons, alkadiendioic acid of 5 to 12 carbons, pentadienoic acid, isoprenoic acid, hexadiendioic acid, partially hydrolyzed polyacrylonitrile, esters thereof, alkenes of 2 to 10 carbons, aromatic alkenes of 8 to 20 carbons and any combination thereof.

5. The hair coloring composition of claim 1, wherein the cationic polymers of composition A and the pretreatment composition are maintained at between 3 and 10.

6. The hair coloring composition of claim 1, wherein anionic polymer of composition B is maintained at a basic pH.

7. The hair coloring composition of claim 1, wherein the pigment microparticles are irregularly and/or regularly shaped, comprise at least one pigment color; and the composition has a solids content of about 0.1 wt % to about 80 wt % preferably about 0.1 wt % to about 40 wt %, more preferable about 0.1 wt % to about 10 wt %, relative to the total weight of the composition.

8. The hair coloring composition of claim 1, wherein the medium of composition A, the pretreatment composition and the medium of composition B is water or an alcoholic aqueous solution.

9. The hair coloring composition of claim 1, wherein the pigment microparticles have a D50[vol] particle diameter between 0.001 microns and 0.5 microns.

10. The hair coloring composition of claim 1, wherein:
the anionic polymer of composition B is a carboxylic acid polymer comprising a carboxylic acid homopolymer or copolymer or terpolymer;
the homopolymer comprises monomeric units of olefinic carboxylic acid, (meth)acrylic acid and optional carboxyl derivatives thereof;
the copolymer or terpolymer comprises monomeric units of (meth)acrylic acid and monomeric units selected from the groups consisting of one or more carboxylate esters, (meth)acrylate esters, one or more (meth)acrylamides, carboxyl derivatives of (meth)acrylic acid and monomeric units of neutral olefins and any combination thereof;
the carboxylic acid polymer has an acid value of from about 0.01 to about 700;
the carboxylic acid polymer has a glass transition temperature in the solid state of from about 60° C. to about 90° C.; and
the carboxylic acid polymer has a weight average molecular weight in the range of about 300 Da to about 10 MDa.

11. The hair coloring composition of claim 1, wherein the cationic polymers of composition A and the pretreatment composition independently are a linear or branched polymer comprising polyethyleneimine, polyallylamine, polydiallyldimethylammonium chloride, polyvinylamine, (vinylamine-styrene) copolymer, poly(omega-aminoalkyl(meth)acrylate), polyvinylpyrrolidine or random or block copolymers thereof.

12. The hair coloring composition of claim 1, wherein the polymer of composition B is an olefinic ester polymer with 1 mole percent to 30 mole percent pendant carboxyl groups.

13. The hair coloring composition of claim 1, wherein the anionic polymer of composition B is dissolved or dispersed in the medium.

14. The hair coloring composition of claim 1, wherein the cationic polymers of the composition A and the pretreatment composition are dissolved or dispersed in the medium.

15. The hair coloring composition of claim 1, wherein the cationic polymer is maintained in ionic form by protonation or as a quaternary ammonium polymer.

16. The hair coloring composition of claim 1, wherein the anionic polymer is maintained in ionic form by salt formation with ethanolamine or with a hydroxide of ammonia, sodium, potassium.

17. The hair coloring composition of claim 1, wherein the pigment microparticies are present in composition A and are maintained in the medium as a dispersion by the cationic polymer and optionally by a suspending agent.

18. The hair coloring composition of claim 1, wherein the medium comprises water.

19. The hair coloring composition of claim 1, wherein the medium comprises water and a polar, protic organic solvent.

20. The hair coloring composition of claim 19, wherein the polar, protic organic solvent is selected from the group consisting of an alkanol of 1 to 3 carbons and the weight percentage of polar, protic solvent is from about 5 wt % to about 25 wt % relative to the total weight of the medium.

21. The hair coloring composition of claim 1, further comprising a plasticizer in one or both of compositions A and B.

* * * * *